(12) United States Patent
Sears et al.

(10) Patent No.: US 9,820,981 B2
(45) Date of Patent: Nov. 21, 2017

(54) TREATMENT OF RETINOPATHY OF PREMATURITY (ROP)

(71) Applicant: The Cleveland Clinic Foundation, Cleveland, OH (US)

(72) Inventors: Jonathan E. Sears, Shaker Heights, OH (US); George B. Hoppe, Cleveland Heights, OH (US); Suzy Yoon, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 15/105,861

(22) PCT Filed: Dec. 19, 2014

(86) PCT No.: PCT/US2014/071595
§ 371 (c)(1),
(2) Date: Jun. 17, 2016

(87) PCT Pub. No.: WO2015/095757
PCT Pub. Date: Jun. 25, 2015

(65) Prior Publication Data
US 2016/0317523 A1    Nov. 3, 2016

Related U.S. Application Data

(60) Provisional application No. 61/918,458, filed on Dec. 19, 2013.

(51) Int. Cl.
*A61K 31/472* (2006.01)
*A61K 31/00* (2006.01)
(52) U.S. Cl.
CPC ............ *A61K 31/472* (2013.01); *A61K 31/00* (2013.01)

(58) Field of Classification Search
CPC .............................. A61K 31/472; A61K 31/00
See application file for complete search history.

(56) References Cited

U.S. PATENT DOCUMENTS

2004/0254215 A1    12/2004    Arend et al.
2012/0282353 A1    11/2012    Roth et al.

OTHER PUBLICATIONS

Nakamura, I. et al. Transition-Metal-Catalyzed Reactions in Heterocyclic Synthesis. Chem. Rev. 2004, vol. 104, p. 2127.*

(Continued)

*Primary Examiner* — Savitha Rao
(74) *Attorney, Agent, or Firm* — Hamilton, Brook, Smith & Reynolds, P.C.

(57) ABSTRACT

Disclosed herein are methods of treating retinopathy of prematurity (ROP) in a premature and/or low birth weight infant in need thereof, comprising administering to the infant an effective amount of a compound represented by Structural Formula I, Structural Formula Ia or Structural Formula II described herein, or a pharmaceutically acceptable salt thereof. Also disclosed herein are methods of inhibiting the destruction of retinal blood vessels in a premature and/or low birth weight infant in need thereof, comprising administering to the infant an effective amount of a compound represented by Structural Formula I, Structural Formula Ia or Structural Formula II, or a pharmaceutically acceptable salt thereof. Also disclosed herein are methods of treating hyperoxia in a premature and/or low birth weight infant in need thereof, comprising administering to the infant an effective amount of a compound represented by Structural Formula I, Structural Formula Ia or Structural Formula II, or a pharmaceutically acceptable salt thereof. By using the methods disclosed herein, particularly when an infant is hyperoxic, oxygen toxicity to the retina of the eye can be inhibited without restricting oxygen supple- (Continued)

mentation, which is often necessary to sustain the life of premature infants.

18 Claims, 7 Drawing Sheets

(56) References Cited

OTHER PUBLICATIONS

Anderson (Chem and Biol 10:787-797, 2003.*
Thiel (Nature Biotechnol 2:513-519, 2004), "libraries are small and hit rates are on the order of one in ten" (p. 517, col. 2.*
Anonymous, FibroGen to Present Phase 2 Data for FG-4592, An Oral Hypoxia-Inducible Factor Prolyl Hydroxylase Inhibitor (HIF-PHI) American Scoiety of Nephrology (ASN) Kidney Week 2012 (Oct. 31, 2012). [Retrieved from internet URL: http://www.businessswire.com/news/home/20121031006644/en/FibroGen-Present-Phase-2-Data-FG-4592-Oral#.V0IfU20wVAs retrieved on Feb. 16, 2015].
Asikainen, T. M. et al., "Activation of hypoxia-inducible factors in hyperoxia through prolyl 4-hydroxylase blockade in cells and explants of primate lung ", *Proceedings of the National Academy of Sciences, USA*, 102: 10212-10217 (2005).
Bruick, R. K. and McKnight, S. L., "A conserved family of prolyl-4-hydroxylases that modify HIF", *Science*, 294: 1337 (Nov. 9, 2001).
Camenisch, G. et al., "ANGPTL3 stimulates endothelial cell adhesion and migration via integrin alpha vbeta 3 and incudes blood vessel formation in vivo", *The Journal of Biological Chemistry*, 277: 17281-17290 (2002).
Claiborn, K., et al., "G. Kaelin Jr. and Gregg L. Semenza receive the 2012 ASCI/Stanley J. Korsmeyer Award", *The Journal of Clinical Investigation*, 122: 1136 (Apr. 2, 2012).
Duan, L. J. et al, "Prolyl hydroxylase domain protein 2 (PHD2) mediates oxygen-induced retinopathy in neonatal mice", *The American Journal of Pathology*, 178: 1881 (Apr. 2011).
Eckle, T. et al., Hypoxia-indicuble factor-1 is central to cardioprotection: a new paradigm for ischemic preconditioning, *Circulation*, 118: 166 (Jul. 8, 2008).
Epstein; A. C. et al., "C. elegans EGL-9 and mammalian homologs define a family of dioxygenases that regulate HIF by prolyl hydroxylation", *Cell*, 107: 43 (Oct. 5, 2001).
Hartnett, M. E. and Lane, R. H., "Effects of oxygen on the development and severity of retinopathy of prematurity", *Journal of AAPOS: the official publication of the American Association for Pediatric Ophthalmology and Strabismus/American Association for Pediatric Ophthalmology and Strabismus*, 17: 229 (Jun. 2013).
Hartnett, M. E. and Penn, J. S., "Mechanisms and management of retinopathy of prematurity", *N Engl J Med*, 367: 2515-2526 (Dec. 27, 2012).
Hoppe, G. et al., "Inducing a visceral Organ to Protect a Peripheral Capillary Bed: Stabilizing Hepatic HIF-1alpha Prevents Oxygen-Induced Retinopathy", *The American Journal of Pathology* (Jun. 2014).
Huang, H. et al., "Reduced retinal neovascularization, vascular permeability, and apoptosis in ischemic retinopathy in the absence of prolyl hydroxylase-1 due to the prevention of hyperoxia-induced vascular obliteration", *Investigative Ophthalmology & Visual Science*, 52: 7565 (Sep. 2011).
Ivan, M. et al., "HIFalpha targeted for VHL-mediated destruction by proline hydroxylation: implications for O2 sensing", *Science*, 292: 464 (Apr. 20, 2001).
Jaakkola, P. et al., "Targeting of HIF-alpha to the von Hippel-Lindau ubiquitylation complex by O2-regulated prolyl hydroxylation", *Science*, 292: 468 (Apr. 20, 2001).
Jiang, B. H. et al, "Dimerization, DNA binding and transactivation properties of hypoxia-inducible factor 1", *Journal of Biological Chemistry*, 271: 17771 (Jul. 26, 1996).

Manalo, D. J. et al., "Transcriptional regulation of vascular endothelial cell responses to hypoxia by HIF-1", *Blood*, 105: 659 (Jan. 15, 2005).
Masson, N. et al., "Independent function of two destruction domains in hypoxia-inducible factor-alpha chains activated by prolyl hydroxylation", *The EMBO Journal*, 20: 5197 (Sep. 17, 2001).
Mole, D. R. et al., "2-oxoglutarate analogue inhibitors of HIF prolyl hydroxylase", *Bioorganic & Medicinal Chemistry Letters*, 13: 2677-2680 (2003).
Moy, B., "Arresting infant retinopathy", *Science Business Exchange*, 2(2): doi: 10.1038/scibx.2009.40 (Jan. 15, 2009).
Notification Concerning Transmittal of International Preliminary Report on Patentability for International Application No. PCT/US2014/071595, "Treatment Of Retinopathy Of Prematurity (ROP)", dated Jun. 30 2016.
Notification of Transmittal of the International Search Report and The Written Opinion of the International Searching Authority for International Application No. PCT/US2014/071595, "Treatment Of Retinopathy Of Prematurity (ROP)", dated Mar. 18, 2015.
Park, S. T. and Maltepe, E., "Hypoxia-inducible factor (HIF) and HIF-stabilizing agents in neonatal care" *Semin Fetal Neonatal Med*, 15: 196 (Jul. 4, 2010).
Rankin, E. B. et al., "Hypoxia-inducible factor-2 (HIF-2) regulates hepatic erythropoietin in vivo", *The Journal of Clinical Investigation*, 117: 1068 (Apr. 2007).
Ratan, R. R. et al., Small molecule activation of adaptive gene expression: tilorone or its analogs are novel potent activators of pypoxia inducible factor-1 that provide prophylaxis against stroke and spinal cord injury, *Annals of the New York Academy of Sciences*, 1147: 383 (Dec. 2008).
Rose, N. R. et al., "Inhibition of 2-oxoglutarate dependent oxygenases", *Chem Soc Rev*, 40: 4364-4397 (2011).
Safran, M. et al., "Mouse model for noninvasive imaging of HIF prolyl hydroxylase activity: Assessment of an oral agent that stimulates erythropoietin production", *Proc Natl Acad Scie USA*, 103: 105-110 (2006).
Sarkar, K. et al., "Adenoviral transfer of HIF-1alpha enhances vascular responses to critical limb ischemic in diabetic mice", Proceedings of the National Academy of Sciences of the United States of America, 106: 18769 (Nov. 3, 2009).
Schofield, C. J. and Ratcliffe, P. J., "Oxygen sensing by HIF hydroxylases", *Nat Rev Mol Cell Biol.*, 5: 343-354 (2004).
Sears, J. E. and Hoppe, G., "Stimulating retinal blood vessel protection with hypoxia-inducible factor stabilization: identification of novel small-molecule hydrazones to inhibit hypoxia-inducible factor prolyl hydroxylase" (an American ophthalmological society thesis), Transactions of the American Ophthalmological Society, 111: 169-179 (2013).
Sears, J. E. et al., "Prolyl Hydroxylase inhibition during hyperoxia prevents oxygen-induced retinopathy", Proceedings of the National Academy of Sciences 105(50): 19898-19903 (Dec. 16, 2008).
Semenza, G. L. and Wang, G. L., "A nuclear factor induced by hypoxia via de novo protein synthesis binds to the human erythropoietin gene enhancer at a site required for transcriptional activiation", *Molecular and Cellular Biology*, 12: 5447 (Dec. 1992).
Semenza, G. L. et al., "Hypoxia-inducible nuclear factors bind to an enhancer element located 3' to the human erythropoietin gene", Proceedings of the National Academy of Sciences of the United States of America, 88: 5680-5684 (1991).
Semenza, G. L., "Hypoxia-inducible factor 1: master regulator of O2 homeostasis", *Curr Opin Genet Dev*, 8: 588 (Oct. 1998).
Siddiq, A. et al., "Selective inhibition of pypoxia-inducible factor (HIF) prolyl-hydroxylase 1 mediates neuroprptoection against normoxic oxidative death via HIF- and CREB-independent pathways", *The Journal of Neuroscience: the official journal of the Society for Neurosicence*, 29: 8828 (Jul. 8, 2009).
Takeda, K. et al., "Prolyl hydroxylase domain protein 2 in oxygen homeostatis of the adult vascular system", *Circulation*, 116: 774-781 (2007).
Trichonas, G. et al., "Prolyl Hydroxylase Inhibition During Hyperoxia Prevents Oxygen-Induced Retinopathy in the Rat 50/10 Model", *Investigative Ophthalmology & Visual Science*, 54(7): 4919-4926 (Jul. 22, 2013).

(56) References Cited

OTHER PUBLICATIONS

Wang, G. L. and Semenza, G. L., "General involvement of hypoxia-inducible factor 1 in transcriptional response to hypoxia", *Proceedings of the National Academy of Sciences of the United States of America*, 90: 4304-4308 (May 1, 1993).

Wiliam, C. et al., HIF prolyl hydroxylases in the rat; organ distribution and changes in expression following hypoxia and coronary artery ligation, *Journal of Molecular and Cellular Cardiology*, 41: 68 (Jul. 2006).

Yu, F. et al., HIF-1α binding to VHL is regulated by stimulus-sensitive proline hydroxylation, *Proceedings of the National Academy of Sciences of the United States of America*, 98: 9630-9635(Aug. 14, 2001).

* cited by examiner

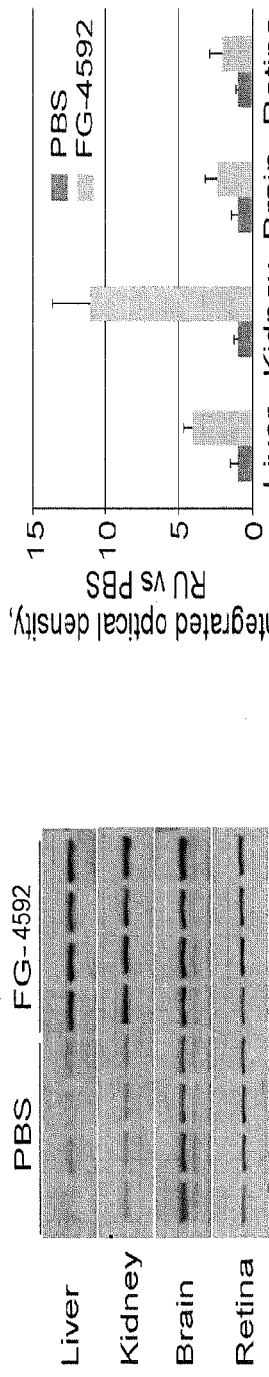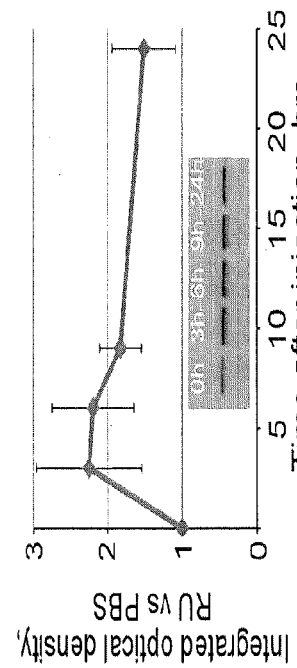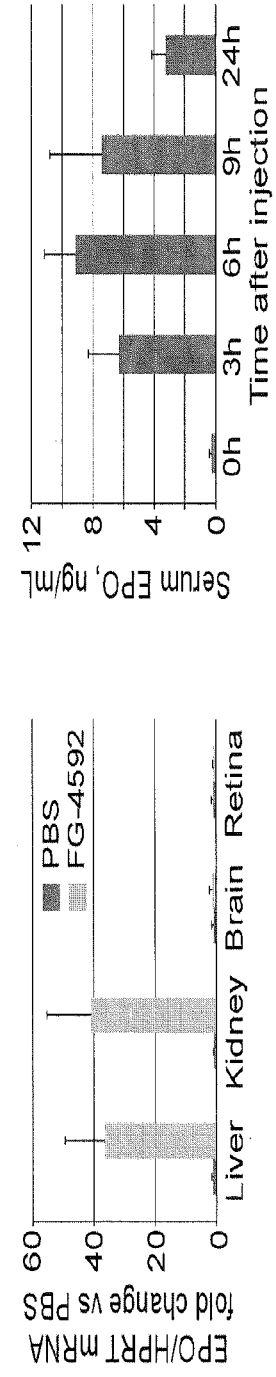
FIG. 5A
FIG. 5B
FIG. 5C
FIG. 5D
FIG. 5E

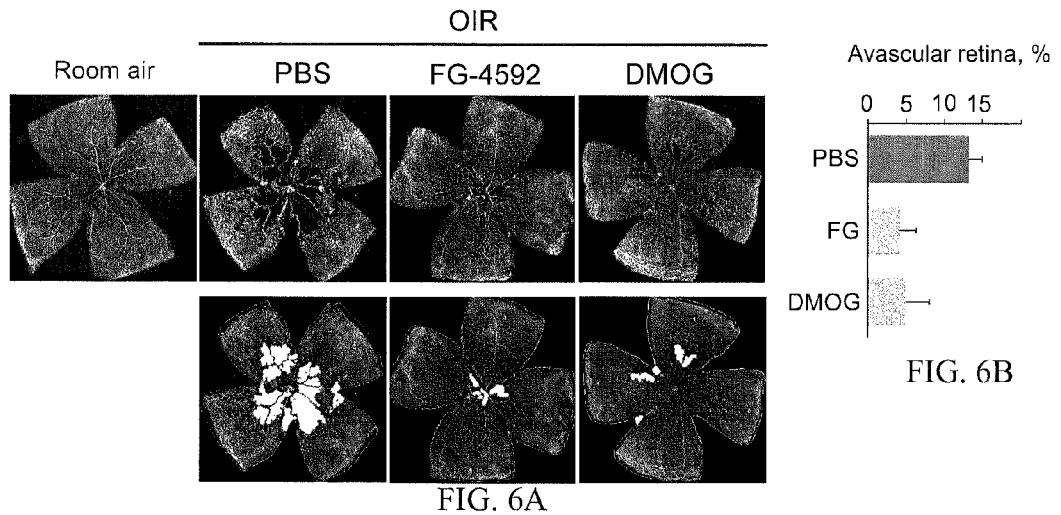
FIG. 6A
FIG. 6B
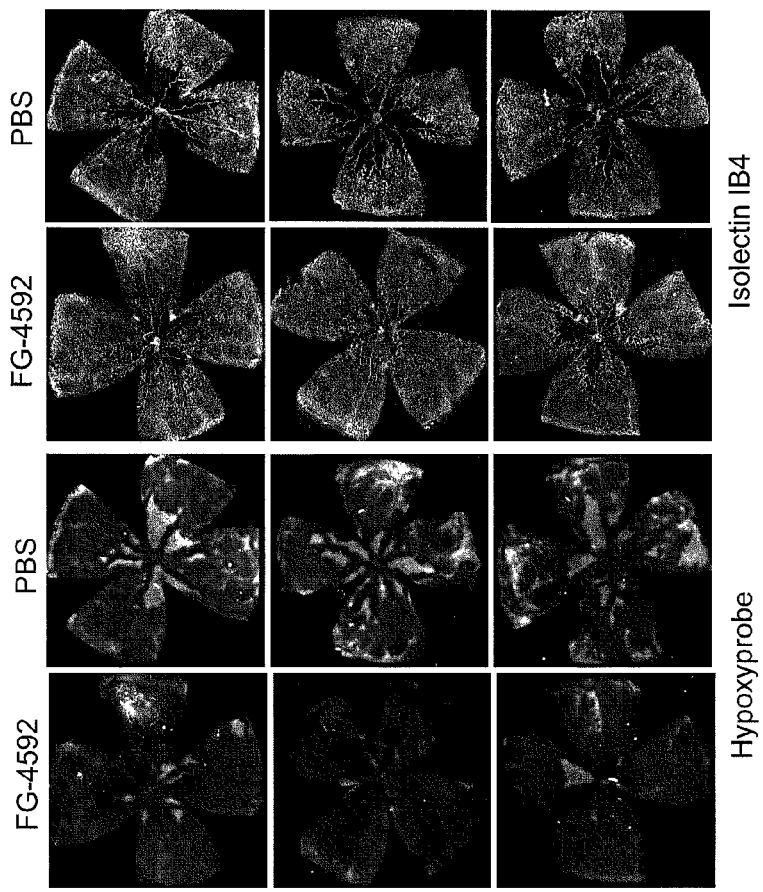
FIG. 6C

TREATMENT OF RETINOPATHY OF PREMATURITY (ROP)

RELATED APPLICATION

This application is the U.S. National Stage of International Application No. PCT/US2014/071595, filed Dec. 19, 2014, which designates the U.S., published in English, and claims the benefit of U.S. Provisional Application No. 61/918,458, filed Dec. 19, 2013. The entire teachings of these applications are incorporated herein by reference.

BACKGROUND OF THE INVENTION

In humans, development of the retinal vasculature occurs in relative hypoxia in utero and is complete at the time of birth. Premature birth interrupts this process and places the premature child at risk for multiorgan damage due to a simple paradox of oxygen—oxygen is necessary to keep premature infants alive, but is toxic to premature developing tissues, including the pre-term retina.

Retinopathy of prematurity (ROP) is a retinovascular disease of premature infants characterized by neovascularization at the intersection of developed, vascularized retina and undeveloped avascular retina. ROP is the most common cause of childhood blindness, and has two phases, based on the oxygen-regulated expression of vascular endothelial growth factor (VEGF). Phase I begins at birth when the infant is placed into hyperoxia, which results in a reduction in the secretion of VEGF that is associated with oxygen-induced vascular obliteration. Phase II is a hypoxic state created by weaning of oxygen supplementation and increased retinal metabolic demand exacerbated by vessel loss from phase I. Phase II is characterized by an overexpression of growth factors, such as VEGF, in the ischemic retina, resulting in pathologic neovascularization.

Although much attention has been focused on the treatment of the angiogenic phase by VEGF and hypoxia-inducible factor 1α (HIF-1α) inhibitors, these treatments do not inhibit the destruction of retinal blood vessels. Thus, there is a need for treatments for hyperoxia-associated conditions that allow for normal retinovascular development in premature infants and inhibit the development of hypoxia-induced neovascularization and phase II of the disease.

SUMMARY OF THE INVENTION

The present invention is based on the discovery that stabilization of hypoxia-inducible factor 1α (HIF-1α) in premature infants during hyperoxia inhibits the destruction of retinal blood vessels and the associated disease, retinopathy of prematurity (ROP). HIF-1α and, in particular, hepatic HIF-1α, can be stabilized by inhibition of hypoxia-inducible factor prolyl hydroxylase (PHD) using systemic PHD inhibitors, such as those described herein. The inhibitors described herein can be used to treat ROP.

One embodiment of the invention is a method of treating ROP in a premature and/or low birth weight infant in need thereof, comprising administering to the infant an effective amount of a compound represented by Structural Formula I, Structural Formula Ia or Structural Formula II, or a pharmaceutically acceptable salt thereof, wherein the values for $R^1$, $R^2$, $R^3$, $R^4$, $R^5$, R" and R'" (as needed in Formulas I and Ia) are as defined and described herein.

In a particular embodiment, the compound administered for treating ROP is represented by Structural Formula II:

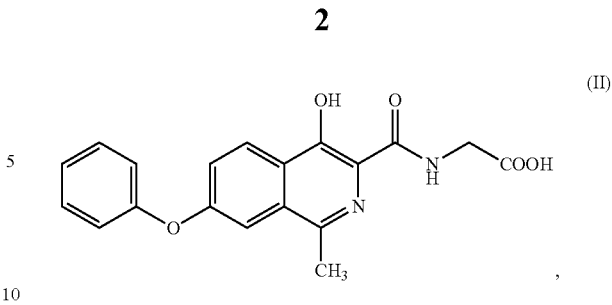

or a pharmaceutically acceptable salt thereof. The compound of Structural Formula II is commonly known in the art as FG-4592.

In another particular embodiment, administration of the compound of Formula I, Formula Ia or Formula II or the pharmaceutically acceptable salt thereof is performed during phase I of ROP.

In another particular embodiment, administration of the compound of Formula I, Formula Ia or Formula II or the pharmaceutically acceptable salt thereof is performed while the premature and/or low birth weight infant is in a hyperoxic state.

In further particular embodiment, the method of treating ROP further comprises co-administration of supplemental oxygen to the premature and/or low birth weight infant. In a specific aspect of this embodiment, administration of the compound of Formula I, Formula Ia or Formula II or the pharmaceutically acceptable salt thereof is performed during phase I of ROP.

Another embodiment of the invention is a method of inhibiting the destruction of retinal blood vessels in a premature and/or low birth weight infant in need thereof, comprising administering to the infant an effective amount of a compound represented by Structural Formula I, Structural Formula Ia or Structural Formula II or a pharmaceutically acceptable salt thereof, wherein the values for $R^1$, $R^2$, $R^3$, $R^4$, $R^5$, R" and R'" (as needed in Formulas I and Ia) are as defined and described herein.

In a particular embodiment, the compound administered for inhibiting the destruction of retinal blood vessels is represented by Structural Formula II, or a pharmaceutically salt thereof.

In another particular embodiment, administration of the compound of Formula I, Formula Ia or Formula II or the pharmaceutically acceptable salt thereof is performed while the premature and/or low birth weight is in a hyperoxic state.

In another particular embodiment, the method of inhibiting destruction of retinal blood vessels further comprises co-administration of supplemental oxygen to the premature and/or low birth weight infant.

Yet another embodiment of the invention is a method of treating hyperoxia in a premature and/or low birth weight infant in need thereof, comprising administering to the infant an effective amount of a compound represented by Structural Formula I, Structural Formula Ia or Structural Formula II or a pharmaceutically acceptable salt thereof, wherein the values for $R^1$, $R^2$, $R^3$, $R^4$, $R^5$, R" and R'" (as needed in Formulas I and Ia) are as defined and described herein.

In a particular embodiment, the compound administered for treating hyperoxia is represented by Structural Formula II, or a pharmaceutically acceptable salt thereof.

In another particular embodiment, administration of the compound of Formula I, Formula Ia or Formula II or the pharmaceutically acceptable salt thereof is performed while the premature and/or low birth weight is in a hyperoxic state.

In a further particular embodiment, the method of treating hyperoxia further comprises co-administration of supplemental oxygen to the premature and/or low birth weight infant.

By using the methods disclosed herein, particularly while an infant is in a hyperoxic state, oxygen toxicity to the retina of the eye can be inhibited without restricting oxygen supplementation, which is necessary to sustain the life of severely premature infants. In particular, FG-4592 has been shown to preserve retinal vessels and inhibit hyperoxia-associated damage and ROP in mice.

BRIEF DESCRIPTION OF THE DRAWINGS

The foregoing will be apparent from the following more particular description of example embodiments of the invention, as illustrated in the accompanying figures.

FIG. 5A is images of Western blots detecting HIF-1α protein in organ lysates derived from mouse pups treated with PBS or FG-4592.

FIG. 5B is a graph of integrated optical density of the immunoblots in FIG. 5A.

FIG. 5C is an image of a Western blot detecting HIF-1α in liver lysate derived from mouse pups injected with FG-4592 and harvested after the indicated period of time, and the corresponding graph of integrated optical density of the immunoblot.

FIG. 5D is a graph of organ-specific erythropoietin (EPO) mRNA expression in mouse pups treated with PBS or FG-4592 by intraperitoneal injection.

FIG. 5E is a graph of EPO protein concentration in serum derived from mouse pups injected with FG-4592 and harvested after the indicated period of time.

FIG. 6A is images of flatmounts from mouse pups receiving a sham PBS injection or an injection of DMOG or FG-4592 (top panel) and the corresponding flatmounts with computer-assisted area calculation to show the avascular region of the flatmounts at postnatal day 17 (P17) (bottom panel). The light-colored shading in the flatmounts in the bottom panel is the area corresponding to the computer-assisted area calculation, and indicates reduction of oxygen-induced vasoobliteration and protection due to FG-4592 or DMOG.

FIG. 6B is a graph and shows the quantification and statistical analysis of the retinal flatmounts of the bottom panel of FIG. 6A, calculated as percent avascular area of total retinal area.

FIG. 6C is images of retinal flatmounts from mouse pups receiving a sham PBS injection or an FG-4592 injection and stained simultaneously for isolectin and Hypoxyprobe, and shows a decrease in ischemic, hypoxic retina at P17 after FG-4592 injection. Three representative replicates for each experimental condition are shown.

DETAILED DESCRIPTION OF THE INVENTION

Figure 1:
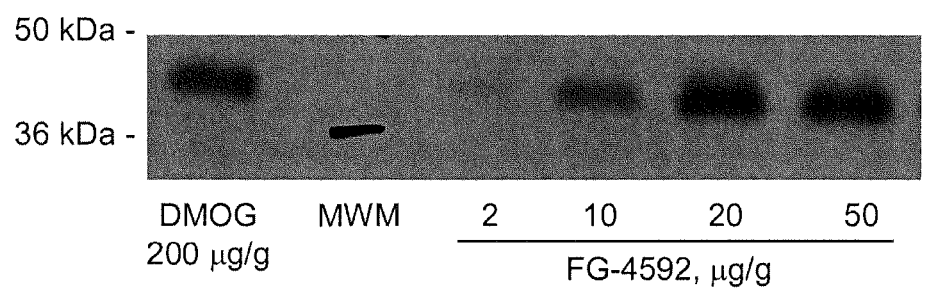
FIG. 1 is an image of an immunoblot detecting serum erythropoietin (Epo), and shows the serum response of Epo, a HIF-regulated gene product, 6 hours after a single, intra-peritoneal injection of the indicated concentration of dim-ethyl oxaloylglycine (DMOG) or FG-4592. Epo is not necessarily related to the beneficial effect of HIF-1α stabilization but rather reflects a downstream gene product of HIF and thereby serves to demonstrate the stabilization of HIF-1α itself.

A description of example embodiments of the invention follows.

Compounds for Use in the Methods of the Invention

Compounds represented by Structural Formula I, Structural Formula Ia or Structural Formula II or a pharmaceutically acceptable salt thereof and used herein are described as below.

A compound represented by Structural Formula I:

$$\text{(I)}$$

[Structure with substituents $R^5$, $R''''$, $R^3$, $R^2$, $R^4$, $R^1$, $R''$, and a $-C(O)-N(R'')-CH_2-COOH$ group on an isoquinoline scaffold]

or a pharmaceutically acceptable salt thereof.

In a first embodiment of the compound of Structural Formula I:

$R^1$ is selected from the group consisting of hydrogen, alkyl, alkoxy, amino, substituted amino, aminoacyl, aryl, halo, heteroaryl, heterocyclyl and $-XR^6$;

X is oxygen, $-S(O)_n-$ or $-NR^7-$;

n is 0, 1 or 2;

$R^6$ is selected from the group consisting of alkyl, aryl, cycloalkyl, heteroaryl and heterocyclyl; and $R^7$ is hydrogen, alkyl or aryl; or $R^6$ and $R^7$, together with the nitrogen atom to which they are commonly bound, form a heterocyclyl;

$R^2$ and $R^3$ are independently selected from the group consisting of hydrogen, alkyl, aryl, heteroaryl, halo, hydroxy, cyano, $-S(O)_m-NR^8-R^8$, $-NR^8C(O)NR^8R^8$ and $-YR^8$, m is 0, 1 or 2;

Y is oxygen, $-S(O)_{m'}-$ or $-NR^9-$;

m' is 0, 1 or 2;

each $R^8$ is independently selected from the group consisting of hydrogen, alkyl, aryl, cycloalkyl, heteroaryl and heterocyclyl; and $R^9$ is selected from the group consisting of hydrogen, alkyl and aryl; or $R^8$ and $R^9$, together with the nitrogen atom to which they are commonly bound, form a heterocyclyl; or $R^2$ and $R^3$, together with their intervening carbon atoms, form an aryl or heteroaryl;

$R^4$ and $R^5$ are independently selected from the group consisting of hydrogen, halo, alkyl, alkoxy, aryl, heteroaryl, and $-ZR^{10}$;

Z is oxygen, $-S(O)_p-$ or $-NR^{11}-$;

p is 0, 1, or 2;

$R^{10}$ is selected from the group consisting of alkyl, aryl, heteroaryl and heterocyclyl; and $R^{11}$ is hydrogen, alkyl or aryl; or $R^{10}$ and $R^{11}$, together with the nitrogen atom to which they are commonly bound, form a heterocyclyl;

R" is hydrogen or alkyl; and

R''' is selected from the group consisting of hydroxy, alkoxy, acyloxy, cycloalkoxy, aryloxy, heteroaryloxy, aryl and $-S(O)_q-R^{12}$;

q is 0, 1 or 2; and $R^{12}$ is selected from the group consisting of alkyl, cycloalkyl, aryl and heteroaryl.

In a first aspect of the first embodiment, $R^1$ is selected from the group consisting of hydrogen, alkyl, alkoxy, aryloxy, aryl, alkylthio, aminoacyl, substituted amino, halo, heteroaryl, heteroaryloxy, $-S(O)_n$-aryl and $-S(O)_n$-heteroaryl. Values for the remaining variables are as defined and described in the first embodiment.

In a second aspect of the first embodiment, $R^1$ is selected from the group consisting of (4-methoxy)phenylsulfonylamino; 2,6-dimethylphenoxy; 3,4-difluorophenoxy; 3,5-difluorophenoxy; 3-chloro-4-fluorophenoxy; 3-methoxy-4-fluorophenoxy; 3-methoxy-5-fluorophenoxy; 4-(methylsulfonamido)phenoxy; 4-(phenylsulfonamido)phenoxy; 4-$CF_3$—O-phenoxy; 4-$CF_3$-phenoxy; 4-chlorophenoxy; 4-fluorophenoxy; 4-(4-fluorophenoxy)phenoxy; 4-methoxyphenoxy; 4-nitrophenoxy; benzyloxy; bromo; butoxy; $CF_3$; chloro; cyclohexyloxy; cyclohexylsulfanyl; cyclohexylsulfonyl; fluoro; hydrogen; iodo; isopropoxy; methyl; phenoxy; phenyl; phenylsulfanyl; phenylsufinyl; phenylsulfonyl; pyridine-1-ylsulfanyl; pyridine-3-yloxy; and pyridine-4-sulfanyl. Values for the remaining variables are as defined and described in the first embodiment, or first aspect thereof.

In a third aspect of the first embodiment, $R^1$ is selected from halo, hydrogen and optionally substituted C1 alkyl. Values for the remaining variables are as defined and described in the first embodiment, or first or second aspect thereof.

In a fourth aspect of the first embodiment, $R^1$ is selected from optionally substituted C1 alkyl. Values for the remaining variables are as defined and described in the first embodiment, or first through third aspects thereof.

In a fifth aspect of the first embodiment, $R^2$ is selected from the group consisting of substituted amino, aryloxy, alkoxy, halo, hydrogen, alkyl, aryl, $-S(O)_m$-aryl, $-S(O)_m$-cycloalkyl, aminocarbonylamino, heteroaryloxy and cycloalkoxy. Values for the remaining variables are as defined and described in the first embodiment, or first through fourth aspects thereof.

In a sixth aspect of the first embodiment, $R^2$ is selected from the group consisting of (4-methoxy)phenylsulfonylamino; 2,6-dimethylphenoxy; 3,4-difluorophenoxy; 3,5-difluorophenoxy; 3-chloro-4-fluorophenoxy; 3-methoxy-4-fluorophenoxy; 3-methoxy-5-fluorophenoxy; 4-(methylsulfonamido)phenoxy; 4-(phenylsulfonamido)phenoxy; 4-$CF_3$—O-phenoxy; 4-$CF_3$-phenoxy; 4-chlorophenoxy; 4-fluorophenoxy; 4-(4-fluorophenoxy)phenoxy; 4-methoxyphenoxy; 4-nitrophenoxy; benzyloxy; bromo; butoxy; $CF_3$; chloro; cyclohexyloxy; cyclohexylsulfanyl; cyclohexylsulfonyl; fluoro; hydrogen; iodo; isopropoxy; methyl; phenoxy; phenyl; phenylsulfanyl; phenylsufinyl; phenylsulfonyl; phenylurea; pyridine-1-ylsulfanyl; pyridine-3-yloxy; and pyridine-4-sulfanyl. Values for the remaining variables are as defined and described in the first embodiment, or first through fifth aspects thereof.

In a seventh aspect of the first embodiment, $R^2$ is optionally substituted phenoxy. Values for the remaining variables are as defined and described in the first embodiment, or first through sixth aspects thereof.

In a second embodiment of the compound of Structural Formula I, the compound of Formula I is represented by Structural Formula Ia:

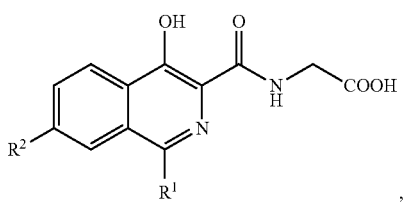

(Ia)

or a pharmaceutically acceptable salt thereof, wherein $R^1$ and $R^2$ are as defined and described in the first embodiment, or any aspect thereof.

In a third embodiment of the compound of Structural Formula I, the compound of Structural Formula I is represented by Structural Formula II:

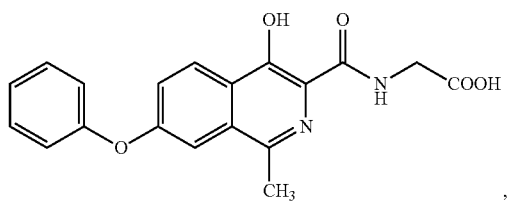

(II)

or a pharmaceutically acceptable salt thereof. The compound of Structural Formula II is also referred to herein as FG-4592.

"Alkyl," as used herein, refers to a saturated branched or straight-chained monovalent hydrocarbon group having 1 to 10 carbon atoms, particularly, 1 to 5 carbon atoms and, more particularly, 1 to 3 carbon atoms. Exemplary alkyl groups include methyl, ethyl, n-propyl, iso-propyl, n-butyl, t-butyl, n-pentyl and the like.

Alkyl can be unsubstituted or substituted with one or more substituents (e.g., 1 to 5 substituents, 1 to 3 substituents) independently selected from the group consisting of alkoxy, acyl, acylamino, acyloxy, amino, substituted amino, aminoacyl, aminocarbonylamino, aminothiocarbonylamino, aminocarbonyloxy, aryl, aryloxy, aryloxyaryl, cyano, halogen, hydroxyl, nitro, oxo, thioxo, carboxyl, carboxyl esters, cycloalkyl, thiol, alkylthio, arylthio, cycloalkylthio, heteroarylthio, heterocyclicthio, heteroaryl, heterocyclyl, cycloalkoxy, heteroaryloxy, heterocyclyloxy, oxycarbonylamino, oxythiocarbonylamino, —OS(O)$_2$-alkyl, —OS(O)$_2$-aryl, —OS(O)$_2$-heteroaryl, —OS(O)$_2$-heterocyclyl, —OS(O)$_2$—NR$^{40}$R$^{40}$, —NR$^{40}$—S(O)$_2$-alkyl, —NR$^{40}$—S(O)$_2$-aryl, —NR$^{40}$—S(O)$_2$-heteroaryl, —NR$^{40}$—S(O)$_2$-heterocyclyl, —NR$^{40}$—S(O)$_2$—NR$^{40}$-alkyl, —NR$^{40}$—S(O)$_2$—NR$^{40}$-aryl, —NR$^{40}$—S(O)$_2$—NR$^{40}$-heteroaryl, and —NR$^{40}$—S(O)$_2$—NR$^{40}$-heterocyclyl, wherein each R$^{40}$ is independently hydrogen or alkyl.

"Alkoxy" refers to the group "alkyl-O—" and includes, by way of example, methoxy, ethoxy, n-propoxy, iso-propoxy, n-butoxy, t-butoxy, sec-butoxy, n-pentoxy and the like. Alkoxy can be unsubstituted or substituted in accordance with alkyl.

"Acyl" refers to the groups H—C(O)—, alkyl-C(O)—, alkenyl-C(O)—, alkynyl-C(O)—, cycloalkyl-C(O)—, aryl-C(O), heteroaryl-C(O)—, and heterocyclyl-C(O)—, provided that a nitrogen atom of the heterocyclyl is not bound to the —C(O)— group, wherein alkyl, alkenyl, alkynyl, cycloalkyl, aryl, heteroaryl, and heterocyclyl are as defined herein.

"Acyloxy" refers to the groups alkyl-C(O)O—, alkenyl-C(O)O—, alkynyl-C(O)O—, aryl-C(O)O—, cycloalkyl-C(O)O—, heteroaryl-C(O)O— and heterocyclyl-C(O)O—, wherein alkyl, alkenyl, alkynyl, aryl, cycloalkyl, heteroaryl and heterocyclyl are as defined herein.

"Aminoacyl" or, as a prefix, "carbamoyl" or "carboxamide," refers to the group —C(O)NR$^{42}$R$^{42}$, wherein each R$^{42}$ is independently selected from the group consisting of hydrogen, alkyl, alkenyl, alkynyl, aryl, cycloalkyl, heteroaryl, and heterocyclyl; or two R$^{42}$, taken together with the nitrogen atom to which they are commonly bound, form a heterocyclyl, wherein alkyl, alkenyl, alkynyl, cycloalkyl, aryl, heteroaryl, and heterocyclyl are as defined herein.

"Alkenyl" refers to a monovalent hydrocarbon group having 1 to 10 carbon atoms and at least one carbon-carbon double bond. Particularly, alkenyl has 2 to 6 carbon atoms and, more particularly, 2 to 4 carbon atoms. Particularly, alkenyl has one or two carbon-carbon double bonds. Alkenyl can be unsubstituted or substituted with 1 to 3 substituents and, particularly, 1 or 2 substituents selected from the group consisting of alkoxy, acyl, acylamino, acyloxy, amino, substituted amino, aminoacyl, aryl, aryloxy, cyano, halogen, hydroxyl, nitro, carboxyl, carboxyl esters, cycloalkyl, heteroaryl, and heterocyclyl.

"Alkynyl" refers to a monovalent hydrocarbon group having 1 to 10 carbon atoms and at least one carbon-carbon triple bond. Particularly, alkynyl has 2 to 6 carbon atoms and, more particularly, 2 to 3 carbon atoms. Alkynyl has at least one and, particularly, one or two carbon-carbon triple bonds. Alkylnyl can be unsubstituted or substituted in accordance with alkenyl.

"Amino" refers to the group —NH$_2$.

"Substituted amino" refers to the group —NR$^{41}$R$^{41}$, wherein each R$^{41}$ group is independently selected from the group consisting of hydrogen, alkyl, alkenyl, alkynyl, cycloalkyl, aryl, heteroaryl, heterocyclyl, —SO$_2$-alkenyl, —SO$_2$-cycloalkyl, —SO$_2$-aryl, —SO$_2$-heteroaryl, and —SO$_2$-heterocyclyl, provided that both R$^{41}$ groups are not hydrogen; or two R$^{41}$, taken together with the nitrogen atom to which they are commonly bound, form a heterocyclyl.

"Acylamino" refers to the groups —NR$^{45}$C(O)alkyl, —NR$^{45}$C(O)cycloalkyl, —NR$^{45}$C(O)alkenyl, —NR$^{45}$C(O)alkynyl, —NR$^{45}$C(O)aryl, —NR$^{45}$C(O)heteroaryl, and —NR$^{45}$C(O)heterocyclyl, wherein R$^{45}$ is hydrogen or alkyl and alkyl, alkenyl, alkynyl, cycloalkyl, aryl, heteroaryl, and heterocyclyl are as defined herein.

"Carbonyloxyamino" refers to the groups —NR$^{46}$C(O)O-alkyl, —NR$^{46}$C(O)O-alkenyl, —NR$^{46}$C(O)O-alkynyl, —NR$^{46}$C(O)O-cycloalkyl, —NR$^{46}$C(O)O-aryl, —NR$^{46}$C(O)O-heteroaryl and —NR$^{46}$C(O)O-heterocyclyl, wherein R$^{46}$ is hydrogen or alkyl and alkyl, alkenyl, alkynyl, cycloalkyl, aryl, heteroaryl, and heterocyclyl are as defined herein.

"Aminocarbonyloxy" or, as a prefix, "carbamoyloxy" refers to the groups —OC(O)NR$^{47}$R$^{47}$, wherein each R$^{47}$ is independently hydrogen, alkyl, alkenyl, alkynyl, cycloalkyl, aryl, heteroaryl or heterocyclyl; or two R$^{47}$, taken together with the nitrogen atom to which they are commonly bound, form a heterocyclyl, wherein alkyl, alkenyl, alkynyl, cycloalkyl, aryl, heteroaryl and heterocyclyl are as defined herein.

"Aminocarbonylamino" refers to the group —NR$^{49}$C(O)NR$^{49}$—, wherein each R$^{49}$ is independently selected from the group consisting of hydrogen and alkyl.

"Aryl" refers to a monovalent aromatic carbocyclic group of from 6 to 14 carbon atoms having a single ring (e.g., phenyl) or multiple condensed rings (e.g., naphthyl or anthryl), which condensed rings may or may not be aromatic (e.g., 2-benzoxazolinone, 2H-1,4-benzoxazin-3(4H)-one-7-yl, and the like) provided that the point of attachment is the aryl group. Exemplary aryls include phenyl and naphthyl.

Aryl can be unsubstituted or substituted with from 1 to 4, for example, 1 to 3, substituents selected from the group consisting of hydroxy, acyl, acylamino, carbonylaminothio, acyloxy, alkyl, alkoxy, alkenyl, alkynyl, amidino, amino, substituted amino, aminoacyl, aminocarbonyloxy, aminocarbonylamino, aminothiocarbonylamino, aryl, aryloxy, cycloalkoxy, heteroaryloxy, heterocyclyloxy, carboxyl, carboxyl esters, cyano, thiol, alkylthio, arylthio, heteroarylthio, cycloalkylthio, heterocyclicthio, cycloalkyl, guanidino, halo, nitro, heteroaryl, heterocyclyl, oxycarbonylamino, oxythiocarbonylamino, —S(O)$_2$-alkyl, —S(O)$_2$-cycloalkyl, —S(O)$_2$-alkenyl, —S(O)$_2$-aryl, —S(O)$_2$-heteroaryl, —S(O)$_2$-heterocyclyl, —OS(O)$_2$-alkyl, —OS(O)$_2$-aryl, —OS(O)$_2$-heteroaryl, —OS(O)$_2$-heterocyclyl, —OSO$_2$—NR$^{51}$NR$^{51}$, —NR$^{51}$S(O)$_2$-alkyl, —NR$^{51}$S(O)$_2$-aryl, —NR$^{51}$S(O)$_2$-heteroaryl, —NR$^{51}$S(O)$_2$-heterocyclyl, —NR$^{51}$S(O)$_2$—NR$^{51}$-alkyl, —NR$^{51}$S(O)$_2$—NR$^{51}$-aryl, —NR$^{51}$S(O)$_2$—NR$^{51}$-heteroaryl, and —NR$^{51}$S(O)$_2$—NR$^{51}$-heterocyclyl, wherein each R$^{51}$ is independently hydrogen or alkyl and the terms are as defined herein.

"Aryloxy" refers to the group aryl-O— and includes, by way of example, phenoxy, napthoxy and the like. Aryloxyl can be unsubstituted or substituted in accordance with aryl.

"Carboxyl" refers to the group —COOH, or salts thereof.

"Carboxyl esters" refers to the groups —C(O)O-alkyl and —C(O)O-aryl, wherein alkyl and aryl are as defined herein.

"Cycloalkyl" refers to cyclic alkyl groups having 3 to 10 carbon atoms. Cycloalkyl can be monocyclic or polycyclic and include, by way of example, adamantyl, cyclopropyl, cyclobutyl, cyclopentyl, cyclohexyl and the like. Cycloalkyl can be unsubstituted or substituted with 1 to 5 substituents selected from the group consisting of oxo (=O), thioxo (=S), alkoxy, acyl, acylamino, acyloxy, amino, substituted amino, aminoacyl, aryl, aryloxy, cyano, halogen, hydroxyl, nitro, carboxyl, carboxyl esters, cycloalkyl, heteroaryl and heterocyclyl.

"Cycloalkoxy" refers to —O-cycloalkyl groups. Cycloalkoxy can be unsubstituted or substituted in accordance with cycloalkyl.

"Halo" or "halogen" refers to fluoro, chloro, bromo and iodo. Particularly, halo is fluoro or chloro.

"Heteroaryl" refers to an aromatic group of 1 to 15 carbon atoms, particularly 1 to 10 carbon atoms, and 1 to 4 heteroatoms selected from the group consisting of oxygen, nitrogen and sulfur. Heteroaryl groups can have a single ring (e.g., pyridinyl or furyl) or multiple condensed rings (e.g., indolizinyl or benzothienyl). Exemplary heteroaryls include pyridinyl, pyrrolyl, indolyl, thiophenyl and furyl. Heteroaryl can be unsubstituted or substituted in accordance with aryl.

"Heteroaryloxy" refers to the group —O-heteroaryl. Heteroaryloxy can be unsubstituted or substituted in accordance with aryl.

"Heterocyclyl" or "heterocyclic" refers to a saturated or unsaturated group having a single ring or multiple condensed rings, from 1 to 10 carbon atoms and from 1 to 4 heteroatoms selected from the group consisting of nitrogen, sulfur and oxygen. In fused ring systems, one or more of the rings can be aryl or heteroaryl, provided that the point of attachment is at the heterocyclyl. Heterocyclyl can be unsubstituted or substituted in accordance with cycloalkyl.

"Heterocyclyloxy" refers to the group —O-heterocyclyl, where heterocyclyl is defined as above. Heterocyclyloxy can be unsubstituted or substituted in accordance with cycloalkyl.

"Thio" refers to the group —SH.

"Alkylthio" refers to the group —S-alkyl, where alkyl is defined as above. Alkylthio can be unsubstituted or substituted in accordance with alkyl.

"Cycloalkylthio" refers to the group —S-cycloalkyl, where cycloalkyl is defined as above. Cycloalkylthio can be unsubstituted or substituted in accordance with cycloalkyl.

"Arylthio" refers to the group —S-aryl, where aryl is defined as above. Arylthio can be unsubstituted or substituted in accordance with aryl.

"Heteroarylthio" refers to the group —S-heteroaryl, where heteroaryl is defined as above. Heteroarylthio can be unsubstituted or substituted in accordance with aryl.

"Heterocyclicthio" refers to the group —S-heterocyclyl, wherein heterocyclyl is defined as above. Heterocyclicthio can be unsubstituted or substituted in accordance with cycloalkyl.

"Hydroxy" refers to the group —OH.

"Phenoxy" refers to the group —O-phenyl, wherein phenyl is unsubstituted or substituted in accordance with aryl.

As used herein, the term "pharmaceutically acceptable salt" refers to those salts which are, within the scope of sound medical judgment, suitable for use in contact with the tissues of infants without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19. Pharmaceutically acceptable salts of the compounds of this invention include those derived from suitable inorganic and organic acids and bases.

Pharmaceutically acceptable salts derived from suitable inorganic and organic acids include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, oxalate, pamoate, pantothenate, phosphate/diphospate, polygalacturonate, salicylate, stearate, subacetate, succinate, sulfate, tannate, tartrate, teoclate, tosylate, and triethiodide salts.

Pharmaceutically acceptable salts derived from suitable inorganic and organic bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Methods of the Invention

One embodiment of the invention is a method of treating ROP in a premature and/or low birth weight infant in need thereof, comprising administering to the infant an effective amount of a compound represented by Structural Formula I, Structural Formula Ia or Structural Formula II, or a pharmaceutically acceptable salt thereof, wherein the values for $R^1$, $R^2$, $R^3$, $R^4$, $R^5$, R" and R'" (as needed in Formulas I and Ia) are as defined and described herein.

In a particular embodiment, the compound administered for treating ROP is represented by Structural Formula II:

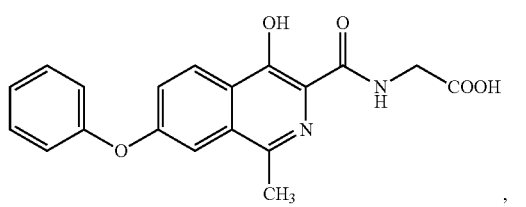

or a pharmaceutically salt thereof.

In another particular embodiment, administration of the compound of Formula I, Formula Ia or Formula II is performed during phase I of ROP.

In yet another particular embodiment, administration of the compound of Formula I, Formula Ia or Formula II or the pharmaceutically acceptable salt thereof is performed while the premature and/or low birth weight infant is in a hyperoxic state.

In a further particular embodiment, the method of treating ROP further comprises co-administration of supplemental oxygen to the premature and/or low birth weight infant. In a specific aspect of this embodiment, administration of the compound of Formula I, Formula Ia or Formula II or the pharmaceutically acceptable salt thereof is performed during phase I of ROP.

Another embodiment of the invention is a method of inhibiting the destruction of retinal blood vessels in a premature and/or low birth weight infant in need thereof, comprising administering to the infant an effective amount of a compound represented by Structural Formula I, Structural Formula Ia or Structural Formula II, or a pharmaceutically acceptable salt thereof, wherein the values for $R^1$, $R^2$, $R^3$, $R^4$, $R^5$, R" and R'" (as needed in Formulas I and Ia) are as defined and described herein.

In a particular embodiment, the compound administered for inhibiting the destruction of retinal blood vessels is represented by Structural Formula II:

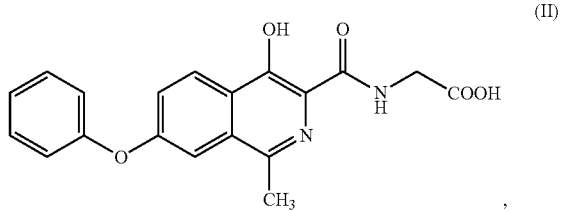 [SMILES: Cc1nc(C(=O)NCC(=O)O)c(O)c2ccc(Oc3ccccc3)cc12]

or a pharmaceutically salt thereof.

In another particular embodiment, administration of the compound of Formula I, Formula Ia or Formula II or the pharmaceutically acceptable salt thereof is performed while the premature and/or low birth weight is in a hyperoxic state.

In yet another particular embodiment, the method of inhibiting destruction of retinal blood vessels further comprises co-administration of supplemental oxygen to the premature and/or low birth weight infant.

Yet another embodiment of the invention is a method of treating hyperoxia in a premature and/or low birth weight infant in need thereof, comprising administering to the infant an effective amount of a compound represented by Structural Formula I, Structural Formula Ia or Structural Formula II, or a pharmaceutically acceptable salt thereof, wherein the values for $R^1$, $R^2$, $R^3$, $R^4$, $R^5$, R" and R'" (as needed in Formulas I and Ia) are as defined and described herein.

In a particular embodiment, the compound administered for treating hyperoxia is represented by Structural Formula II:

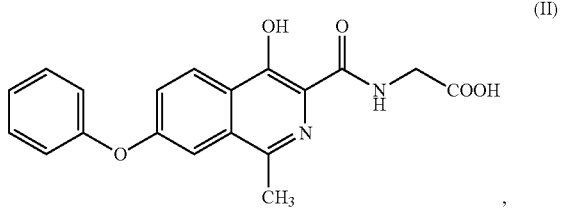 [SMILES: Cc1nc(C(=O)NCC(=O)O)c(O)c2ccc(Oc3ccccc3)cc12]

or a pharmaceutically acceptable salt thereof.

In another particular embodiment, administration of the compound of Formula I, Formula Ia or Formula II or the pharmaceutically acceptable salt thereof is performed while the premature and/or low birth weight infant is in a hyperoxic state.

In a further particular embodiment, the method of treating hyperoxia further comprises co-administration of supplemental oxygen to the premature and/or low birth weight infant.

"Treatment" or "treating," as used herein, refers to partially or totally inhibiting, delaying, or reducing the severity of the symptoms and/or pathology of hyperoxia or ROP in a premature and/or low birth weight infant. The terms "treatment" and "treating" also encompass the prophylactic administration of a compound described herein to a premature and/or low birth weight infant (i.e., infants at risk of becoming hyperoxic or developing ROP) in an effort to reduce the likelihood of the infant becoming hyperoxic or developing ROP or the symptoms and/or pathology of hyperoxia or ROP.

"Hyperoxia," as used herein, refers to a condition in which the body has an excess of oxygen or higher than normal partial pressure of oxygen. Premature birth, low birth weight or oxygen supplementation in premature and/or low birth weight infants can cause hyperoxia. In particular embodiments of the methods disclosed herein, the compound, or pharmaceutically acceptable salt thereof, is administered while the infant is in a hyperoxic state.

As used herein, "retinopathy of prematurity (ROP)" is a retinovascular disease of premature infants characterized by neovascularization at the intersection of developed, vascularized retina and undeveloped avascular retina. ROP is the most common cause of childhood blindness, and has two phases, based on the oxygen-regulated expression of vascular endothelial growth factor (VEGF). Phase I of ROP begins at birth when the infant is placed into hyperoxia, which results in a reduction in the secretion of VEGF that is associated with oxygen-induced vascular obliteration. Phase II of ROP is a hypoxic state created by weaning of oxygen supplementation and increased retinal metabolic demand exacerbated by vessel loss from phase I. Phase II is characterized by an overexpression of growth factors, such as VEGF, in the ischemic retina, resulting in pathologic neovascularization.

"Premature infant," as used herein, refers to one born before 36 weeks gestation. In some embodiments of the methods described herein, the infant is a premature infant. In more particular embodiments, the premature infant is a severely premature infant "Severely premature infant," as used herein, refers to one born before 30 weeks gestation (e.g., infants born before 28 weeks of gestation).

"Low birth weight infant," as used herein, refers to one born weighing under five pounds. In some embodiments of the methods described herein, the infant is a low birth weight infant.

Oftentimes, a premature infant is of a low birth weight. Therefore, in some embodiments of the methods described herein, the infant is both a premature (e.g., severely premature) and a low birth weight infant.

"Effective amount," as used herein, means an amount of a compound described herein that elicits the desired biological response in a premature and/or low birth weight infant. Such response includes alleviation, total or partial, or inhibition, total or partial, of the onset of the symptoms of the disease or condition being treated.

Supplemental oxygen is often necessary to keep premature and/or low birth weight infants alive. Therefore, in some embodiments, the methods described herein further comprise co-administering supplemental oxygen to a premature and/or low birth weight infant. Oxygen saturation levels of premature and/or low birth weight infants can be maintained at about 85% to about 100%, particularly, about 90% to about 95% using oxygen supplementation. Methods of assessing oxygen saturation levels in premature and/or low birth weight infants are well-known in the art.

"Co-administration" emcompasses administration in an essentially simultaneous manner or in a sequential manner sufficiently close in time to have the desired therapeutic effect.

Pharmaceutical Formulations and Administration

Commonly, a compound described herein is administered as a composition or formulation (e.g., a pharmaceutical composition or a pharmaceutical formulation), comprising a compound described herein, or a pharmaceutically acceptable salt thereof, and a pharmaceutically acceptable carrier or diluent.

"Pharmaceutically acceptable carrier or diluent," as used herein, refers to a nontoxic carrier, adjuvant, or vehicle that does not destroy the pharmacological activity of a compound with which it is formulated.

The compounds, and pharmaceutically acceptable salts thereof, and compositions described herein can be formulated for administration by ocular, oral, intranasal, sublingual, transdermal, rectal, topical (with or without occlusion) or intravenous (both bolus and infusion) routes or by injection (ocular, intraperitoneal, subcutaneous, intramuscular, intratumoral, or parenteral, for example, intraperitoneal, subcutaneous, intramuscular, intratumoral, or parenteral), inhalation or insufflation. The compound, or pharmaceutically acceptable salt thereof, or composition may be in a dosage unit, such as a tablet, pill, capsule, powder, granule, liposome, ion exchange resin, sterile ocular solution, or ocular delivery device (such as a contact lens and the like facilitating immediate release, timed release, or sustained release), parenteral solution or suspension, metered aerosol or liquid spray, drop, ampoule, auto-injector device, or suppository.

Although not wishing to be bound by any particular theory, it is believed that the target of systemic HIF-1α stabilization is hepatic HIF-1α. Thus, in particular embodiments, the compound, or pharmaceutically acceptable salt thereof, or composition is administered systemically, for example, by enteral (e.g., oral) administration or parenteral (e.g., intravenous) administration.

In some embodiments of the invention, the compound, or pharmaceutically acceptable salt thereof, or composition is administered orally. Compositions suitable for oral administration include solid forms, such as pills, tablets, caplets, capsules (each including immediate release, timed release, and sustained release formulations), granules and powders, and liquid forms, such as solutions, syrups, elixirs, emulsions and suspensions. For oral administration, the composition is preferably in the form of a tablet or capsule comprising a compound described herein, or a pharmaceutically acceptable salt thereof, as the active agent.

The oral composition is preferably formulated as a homogeneous composition, wherein the active ingredient is dispersed evenly throughout the mixture, which may be readily subdivided into dosage units containing equal amounts of a compound of the invention. The compositions can be prepared by mixing a compound described herein, or a pharmaceutically acceptable salt thereof, with one or more optionally present pharmaceutical carriers (such as a starch, sugar, diluent, granulating agent, lubricant, glidant, binding agent, and disintegrating agent), one or more optionally present inert pharmaceutical excipients (such as water, glycols, oils, alcohols, flavoring agents, preservatives, coloring agents, and syrup), one or more optionally present conventional tableting ingredients (such as corn starch, lactose, sucrose, sorbitol, talc, stearic acid, magnesium stearate, dicalcium phosphate, and any of a variety of gums), and an optional diluent (such as water).

Binder agents include starch, gelatin, natural sugars (e.g., glucose and beta-lactose), corn sweeteners and natural and synthetic gums (e.g., acacia and tragacanth). Disintegrating agents include starch, methyl cellulose, agar, and bentonite.

Tablets and capsules represent an advantageous oral dosage unit form. Tablets can be sugarcoated or film-coated using standard techniques. Tablets can also be coated or otherwise compounded to provide a prolonged, control-release therapeutic effect. The dosage form can comprise an inner dosage and an outer dosage component, wherein the outer component is in the form of an envelope over the inner component. The two components can further be separated by a layer which resists disintegration in the stomach (such as an enteric layer) and permits the inner component to pass intact into the duodenum or a layer which delays or sustains release. A variety of enteric and non-enteric layer or coating materials (such as polymeric acids, shellacs, acetyl alcohol, and cellulose acetate or combinations thereof) can be used.

Compounds described herein can also be administered via a slow release composition, wherein the composition includes a compound described herein, or a pharmaceutically acceptable salt thereof, and a biodegradable slow release carrier (e.g., a polymeric carrier) or a pharmaceutically acceptable non-biodegradable slow release carrier (e.g., an ion exchange carrier).

Biodegradable and non-biodegradable slow release carriers are well known in the art. Biodegradable carriers are used to form particles or matrices which retain an active agent(s) and which slowly degrade/dissolve in a suitable environment (e.g., aqueous, acidic, basic and the like) to release the agent. Such particles degrade/dissolve in body fluids to release the active compound(s) therein. The particles are preferably nanoparticles (e.g., in the range of about 1 to 500 nm in diameter, particularly about 50-200 nm in diameter, and most particularly about 100 nm in diameter).

The compounds of the invention formulated for administration orally in a liquid form can be in the form of an aqueous solution, a suitably flavored syrup, an aqueous or oil suspension, a flavored emulsion with edible oils, such as cottonseed oil, sesame oil, coconut oil or peanut oil and the like, or an elixir or similar pharmaceutical vehicle. Suitable dispersing or suspending agents for aqueous suspensions include synthetic and natural gums such as tragacanth, acacia, alginate, dextran, sodium carboxymethylcellulose, methylcellulose, polyvinyl-pyrrolidone, and gelatin. The liquid forms in suitably flavored suspending or dispersing agents can also include synthetic and natural gums.

The compounds can be administered parenterally via injection. In particular embodiments, the compound, or pharmaceutically acceptable salt thereof, or composition is administered intraperitoneally, intravenously or subcutaneously. For parenteral administration, sterile suspensions and solutions are desired. Thus, formulations useful for parenteral (including intraperitoneal, subcutaneous and intravenous) administration include sterile solutions, emulsions, and suspensions. A parenteral formulation can consist of the active ingredient dissolved in or mixed with an appropriate inert liquid carrier. Acceptable liquid carriers usually comprise aqueous solvents and other optional ingredients for aiding solubility or preservation. Such aqueous solvents include sterile water, Ringer's solution, or an isotonic aqueous saline solution. Other optional ingredients include vegetable oils (such as peanut oil, cottonseed oil, and sesame oil), and organic solvents (such as solketal, glycerol, and formyl). A sterile, non-volatile oil can be employed as a solvent or suspending agent. The parenteral formulation can be prepared by dissolving or suspending the active ingredient in the liquid carrier, whereby the final dosage unit contains from 0.005 to 10% by weight of the active ingredient. Other additives include preservatives, isotonizers, solubilizers, stabilizers, and pain-soothing agents. Injectable suspensions can also be prepared, in which case appropriate liquid carriers, suspending agents and the like can be employed. Isotonic preparations, which generally contain suitable preservatives, are employed when intravenous administration is desired.

The dosage form containing the compound, or pharmaceutically acceptable salt thereof, or the composition contains an effective amount of the active ingredient to provide a therapeutic or prophylactic effect. Dosages will vary depending on factors associated with the particular infant being treated (e.g., age, weight, and time of administration), the severity of the condition being treated, the compound being employed, the mode of administration, and the strength of the preparation. In some embodiments, the compound, or pharmaceutically acceptable salt thereof, is administered at a dose of from about 0.1 mg/kg body weight to about 1,000 mg/kg body weight, for example, from about 1 mg/kg body weight to about 100 mg/kg body weight, from about 100 mg/kg body weight to about 500 mg/kg body weight or from about 0.1 mg/kg body weight to about 25 mg/kg body weight; particularly, from about 1 mg/kg body weight to about 100 mg/kg body weight, for example, from about 5 mg/kg body weight to about 50 mg/kg body weight, from about 1 mg/kg body weight to about 25 mg/kg body weight, from about 25 mg/kg body weight to about 75 mg/kg body weight or from about 50 mg/kg body weight to about 95 mg/kg body weight; and, more particularly, about 10 mg/kg body weight.

It is understood that the amount of compound dosed per day can be administered beginning on the day of birth or shortly thereafter (e.g., on day 10, 9, 8, 7, 6, 5, 4, 3 or 2 of the infant's life) and continuing every day, every other day, every 2 days, every 3 days, every 4 days, every 5 days, every 6 days, every 7 days, etc. For example, with every other day administration, a 10 mg/kg body weight dose can be initiated on Monday with a first subsequent 10 mg/kg body weight dose administered on Wednesday, a second subsequent 10 mg/kg body weight dose administered on Friday, etc. In some embodiments, the compound, or pharmaceutically acceptable salt thereof, or composition is administered at about three to about seven day intervals, for example, about every three days, about every four days, about every five days, about every six days or about every seven days.

Administration can be continued while the infant is in a hyperoxic state, for example, until the infant is weaned off of supplemental oxygen.

Administration can also be continued until the development of the retinal vasculature is complete or is comparable or approximately comparable to the retinal vasculature of a full-term infant, for example, a full-term infant of approximately the same age.

Typically, administration can be continued as long as about 28 days post-birth, for example, for about the first 7 days, the first 14 days, the first 21 days or the first 28 days of the infant's life. In some embodiments, the compound, or pharmaceutically acceptable salt thereof, or composition can be administered for about the first 14 to about the first 28 days of the infant's life, for example, for about the first 16 days of the infant's life.

In particular embodiments, the compound, or pharmaceutically acceptable salt thereof, or composition is administered at about three to about seven day intervals during about the first two to about the first four weeks of the premature and/or low birth weight infant's life. More particularly, the compound, or pharmaceutically acceptable salt thereof, or composition is administered about every four days for about the first sixteen days of the infant's life. Alternatively, the compound, or pharmaceutically acceptable salt thereof, is administered (e.g., by oral or intravenous administration) about every seven days for about the first 21 to about the first 28 days of the infant's life.

The compound, or pharmaceutically acceptable salt thereof, or composition can be administered in a single dose per day or in multiple doses per day. Typically, the compound, or pharmaceutically acceptable salt thereof, or composition is administered once per day, twice per day, three times per day, four times per day or five times per day. For example, the compound, or pharmaceutically acceptable salt thereof, or composition can be administered in a single dose per day every about 3 to about 7 days. When multiple doses per day are used, the amount of each dosage can be the same or different. Typically, when multiple doses per day are used, the timing between each dose is equivalent or substantially equivalent. For example, two doses per day of about 5 mg/kg body weight can be administered with about a 12 hour interval between doses.

EXEMPLIFICATION

HIF-1 is a multimeric oxygen-regulated transcription factor critical to vascular development and maintenance. HIF-1 is a heterodimer composed of inducible $\alpha$ and constitutive $\beta$ subunits. The stability of HIF-1$\alpha$ is regulated by HIF prolyl hydroxylases (PHD), which induces hydroxylation on two proline residues within the oxygen degradation domain (ODD) Inhibition of hypoxia-inducible factor PHD can be induced by oxoglutarate analogs, which competitively inhibit the hydroxylation of HIF-1$\alpha$ by displacing the endogenous oxoglutarate cofactor. Lack of hydroxylation of HIF-1α in the oxygen degradation domain results in prevention of degradation and increased stability of HIF-1α, allowing it to dimerize with its β subunit to form the active HIF complex.

Oxygen, such as that given to premature infants, causes down-regulation of HIF, which causes, in turn, a decrease in VEGF that leads to the vascular obliteration of the developing retina observed during phase I of ROP. The compounds described herein stabilize HIF-1α during hyperoxia, a condition that normally turns off the activity of HIF, thereby promoting more robust upregulation of the proangiogenic molecules VEGF and Epo. This approach inhibits the oxygen-induced vascular obliteration of phase I of ROP as well as the development of hypoxia-induced neovascularization and progression to the proliferative stage of ROP.

FIG. 1 is an image of an immunoblot detecting serum erythropoietin (Epo), and shows the serum response of Epo, a HIF-regulated gene product, 6 hours after a single, intraperitoneal injection of the indicated concentration of DMOG or FG-4592. Quantification of the immunoblot shows that FG-4592 is approximately fifteen times more potent than DMOG. Epo is an excellent marker of HIF-1α stability. Serum was obtained from mouse pups at postnatal day (P) 8 of age, separated by SDS-PAGE, transferred to PVDF, and subjected to immunoblot analysis using an anti-HIF-1α antibody.

Figure 2:
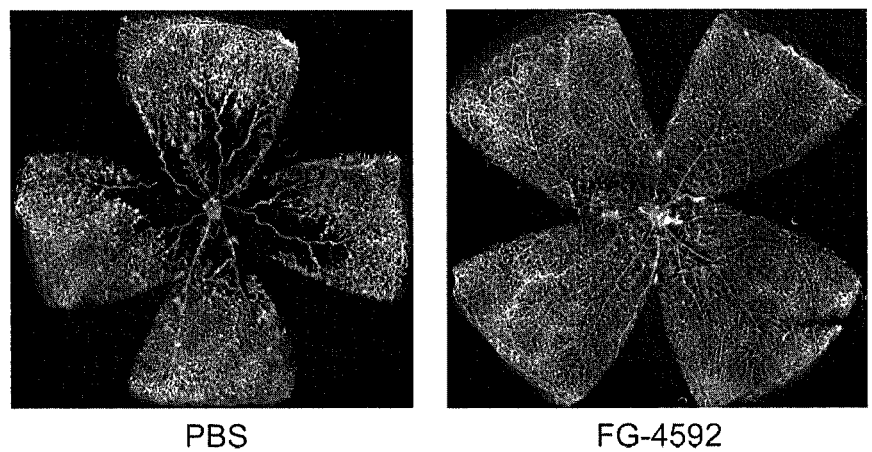
FIG. 2 are retinal flatmounts of oxygen-induced retinopathy (OIR), and shows the preservation of retinal vessels (right panel) in a mouse pup treated with FG-4592 compared to a pup treated with phosphate-buffered saline (PBS) (left panel).

FIG. 2 is retinal flatmounts of oxygen-induced retinopathy (OIR), and shows the preservation of retinal vessels (right panel) in a pup treated with FG-4592 compared to a pup treated with PBS (left panel). The PBS-treated pup has an ischemic, posterior retina compared to the FG-4592-treated pup. Pups were treated with intraperitoneal injection of 10 μg/g body weight FG-4592 at P6, P8, and P10 while in 75% hyperoxia. At P12, pups were removed to room air with their nursing mothers and sacrificed at P17. Eyes were removed and fixed for 15 minutes in fresh 4% paraformaldehyde (PFA) before isolating whole retina, permeabilizing and lectin staining, then flat mounting for fluorescence microscopy.

Figure 3A:
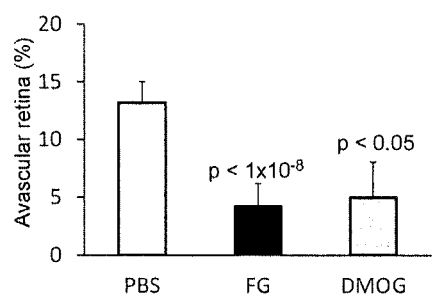
FIG. 3A is a graph of capillary drop-out in a murine OIR model, and shows that FG-4592 (FG) inhibits capillary drop-out better than DMOG, an experimental inhibitor of HIF prolyl hydroxylase (p=10 eyes each group).

FIG. 3A is a quantification of capillary destruction in a murine OIR model, and shows that FG-4592 inhibits capillary drop-out better than DMOG (p=10 eyes each group). An automated computer program (ImagePro version 7.0) measures capillary dropout and neovascular tufting seen in 3B.

Figure 3B:
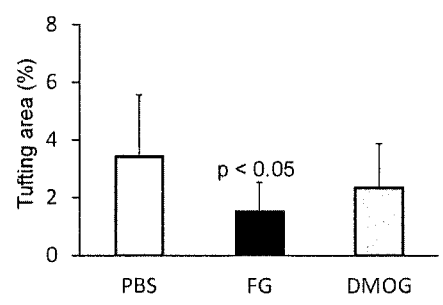
FIG. 3B is a graph of neovascularization in a murine OIR model, and shows that FG-4592 (FG) inhibits neovascularization subsequent to capillary drop-out better than DMOG (p=10 eyes each group).

FIG. 3B is a graph of neovascularization in a murine OIR model, and shows that FG-4592 inhibits neovascularization subsequent to capillary drop-out better than DMOG (p=10 eyes each group).

Proposed Protocol for Clinical Trial with FG-4592

FG-4592 will be administered by oral or intravenous route at a dose of 10 mg/kg every four days for the first 16 days of infant life to premature and/or low birth weight infants (e.g., infants born before 28 weeks gestation), who are being treated with supplemental oxygen at an oxygen saturation between 90% and 95%. The efficacy of FG-4592 will be assessed by dilated ophthalmoscopy at 4 weeks postpartum and every 2 weeks thereafter. Fundus findings will be graded and treated by the international standards of ROP diagnosis and management and the Early Treatment for Retinopathy of Prematurity study. W. V. Good, Final results of the Early Treatment for Retinopathy of Prematurity (ETROP) randomized trial. *Trans Am Ophthalmol Soc* 102, 233 (2004). The Hypoxia Inducible Factor Prolyl Hydroxylase Inhibitor FG-4592 Increases Serum Angiopoietin-Like Protein 3 (ANGPTL-3) and Prevents Oxygen-Induced Retinopathy OIR and Preparation of Retinal Flatmounts.

The mouse model of ROP used in this study is based on a well-established protocol by Smith et al. (L. E. Smith, E. Wesolowski, A. McLellan, S. K. Kostyk, R. D'Amato, R. Sullivan, and P. A. D'Amore. Oxygen-induced retinopathy in the mouse. Investigative ophthalmology & visual science. 35:101-111 (1994)) that involves exposing pups and their nursing mothers to 5 days of hyperoxia (75% oxygen) during P7 through P12 in the wild type C57BL6 (WT) pups. A Plexiglas incubator with an oxygen sensor and feedback system ProOx (Biospherix, Lacona, N.Y.) was used to ensure continuous hyperoxia. Animals were injected intraperitoneally with FG-4592 (10 μg/g), DMOG (200 μg/g) or control PBS in the equivalent volume at P6, P8, and P10. After 5 days of hyperoxia from P7 through P12, the pups were returned to room-air (normoxic) conditions through P17, at which point retinas were isolated for flatmount analysis. Flatmount preparation and lectin (GS-IB4-Alexa568, Life Technologies, Grand Island, N.Y.) staining was performed essentially as described elsewhere (K. M. Connor, N. M. Krah, R. J. Dennison, C. M. Aderman, J. Chen, K. I. Guerin, P. Sapieha, A. Stahl, K. L. Willett, and L. E. Smith. Quantification of oxygen-induced retinopathy in the mouse: a model of vessel loss, vessel regrowth and pathological angiogenesis. Nat Protoc. 4:1565-1573 (2009); A. Stahl, K. M. Connor, P. Sapieha, K. L. Willett, N. M. Krah, R. J. Dennison, J. Chen, K. I. Guerin, and L. E. Smith. Computer-aided quantification of retinal neovascularization. Angiogenesis. 12:297-301 (2009)). Retinas were dissected using four radial cuts, and flatmounted onto glass slides with Vectashield (Vector Labs, Burlingame, Calif.). All animal procedures were performed in accordance with the Cleveland Clinic Institutional Animal Care and Use Committee.

Quantification of Retinal Flatmounts.

For quantitative analysis of avascular area, vascular tortuosity, and tufting, retinal images were batch processed using a customized macro and algorithms generated in Image-Pro Plus 7.0 (Media Cybernetics, Silver Spring, Md.) as previously described (J. E. Sears, G. Hoppe, Q. Ebrahem, and B. Anand-Apte. Prolyl hydroxylase inhibition during hyperoxia prevents oxygen-induced retinopathy. Proceedings of the National Academy of Sciences of the United States of America. 105:19898-19903 (2008)).

Western Blot Analysis.

Mice were sacrificed by ketamine/xylazine overdose, organs collected and placed in RIPA buffer (200 μL per 50 mg of tissue, pH 7.0) containing protease inhibitors Complete (Roche, Indianapolis, Ind.), disrupted using a tight fitting microtube pestle, and centrifuged to remove particulate matter. A Pierce BCA protein assay (Thermo Scientific, Rockford, Ill.) was used to measure protein concentrations. Lysates were subjected to 4-20% SDS-PAGE and electrotransferred to PVDF membranes for immunoblotting. Membranes were blocked with 5% nonfat dried milk in Tris-buffered saline and 0.1% Tween-20, then probed with anti-HIF-1α, antibody (Cayman Chemical, Ann Arbor, Mich.) overnight. After washing and secondary antibody hybridization, membranes were exposed by chemiluminescence (Western Lighting, PerkinElmer, Waltham, Mass.).

Reverse Transcription and Quantitative PCR.

Tissue from liver, kidney, brain and retina were placed into 1 mL of RNAlater reagent (Qiagen, Germantown, Md.) and stored at −80° C. Total RNA was extracted using RNeasy kit (Qiagen) and measured using NanoDrop and standard spectrophotometric parameters. One μg of total RNA from each sample was retrotranscripted to cDNA using QuantiTect Reverse Transcription Kit (Qiagen). One μl of cDNA samples was used as template for amplification reactions carried out with the QuantiTect SYBR Green PCR kit (Qiagen) following the manufacturer's instructions. PCR amplifications were performed in a 7900HT Fast Real-Time PCR system (Applied Biosystems, Foster City, Calif.) and quantitative PCR data analysis was performed with RQ Managed software (Applied Biosystems).

In Vivo Localization of PHD Inhibition.

Gt(ROSA)26Sor$^{tm1(Luc)Kael}$ (luc-ODD) mice were obtained from the Jackson Laboratory (Bar Harbor, Me.). Pups were given i.p. injections of 10 µg/g FG-4592 at indicated periods of time prior to live imaging. Mice were injected with mixture of 100 mg/kg ketamine, 10 mg/kg xylazine and 50 mg/kg luciferin and placed in a light-tight chamber connected to a supercooled, charge-coupled camera. Photons were collected for 15 seconds using IVI 100 Imaging System (PerkinElmer, Waltham, Mass.).

EPO, VEGF, ANGPTL-3 ELISA.

Wild-type (WT) and HIF-1α knock-out (KO) P8 mouse pups were injected with 10 µg/g FG-4592 and, following indicated periods of time, the pups were anesthetized by ketamine/xylazine, blood was drawn using heparinized 27-gauge needle and syringe. Serum was diluted 1:10 (EPO), 1:5 (VEGF) or 1:100 (ANGPTL-3) with sample diluent provided by the manufacturer (R&D Systems, Minneapolis, Minn.). Spectrophotometric measurements of EPO, VEGF, and ANGPTL-3 quantities were obtained according to the manufacturer's instructions.

Results.

FG-4592 was solubilized as a stock solution of 50 µg/ml in DMSO, which was then diluted 50 times in PBS to a concentration of 1 µg/microliter to facilitate a final dose of 10 µg/g body weight of each mouse pup. Three injections were administered during the hyperoxic phase of oxygen-induced retinopathy (OIR) at 48-hour intervals.

Figure 4A:
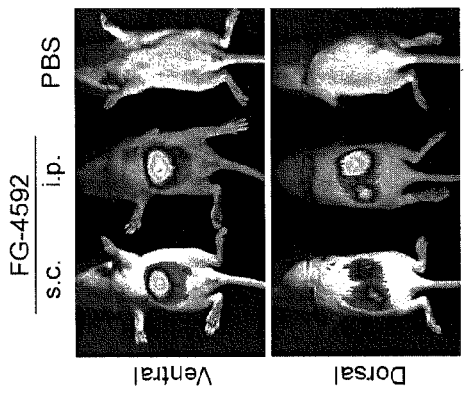
FIG. 4A is ventral and dorsal views of a luciferase-oxygen dependent degradation domain (luc-ODD) mouse treated with PBS or FG-4592 by either subcutaneous (s.c.) or intraperitoneal (i.p.) injection, and shows that both i.p. and s.c. injections create liver- and kidney-specific luminescence in the luc-ODD mouse.

FIG. 4A is ventral and dorsal views of a luciferase-oxygen dependent degradation domain (luc-ODD) mouse treated with PBS or FG-4592 by either subcutaneous (s.c.) or intraperitoneal (i.p.) injection, and shows that both i.p. and s.c. injections create liver- and kidney-specific luminescence in the luc-ODD mouse. The luc-ODD mouse has a transgene comprised of luciferase fused to the ODD and, therefore, serves as a reporter gene in vivo of where hydroxylation of the ODD is inhibited, observed as luminescence in tissue lysates and whole animal imaging.

Figure 4C:
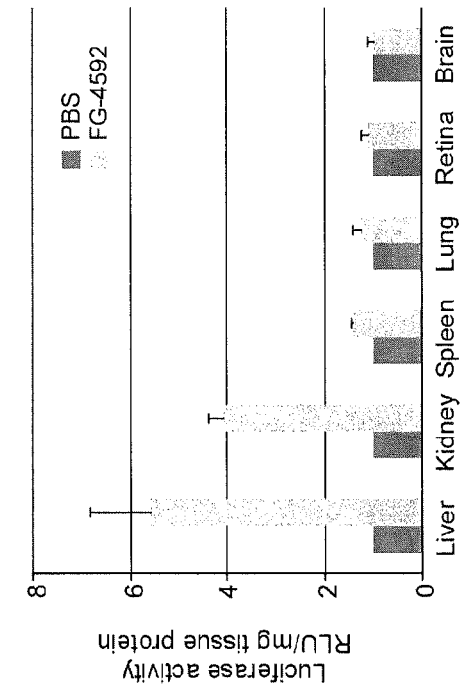
FIG. 4C is a graph of luciferase activity (RLU/mg tissue protein) in organ lysates derived from luc-ODD mice treated with PBS or FG-4592, and shows specificity of FG-4592 for liver and kidney.
Figure 4B:
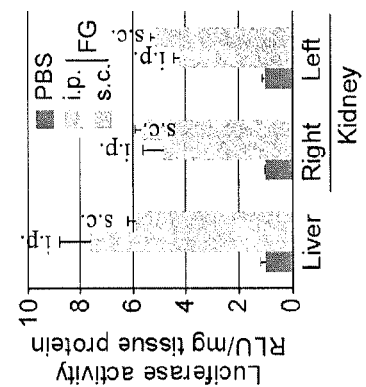
FIG. 4B is a graph of luciferase activity (RLU/mg tissue protein) in liver- and kidney-derived organ lysates derived from luc-ODD mice treated with PBS or FG-4592 by either s.c. or i.p. injection, and shows liver and kidney tropism by both i.p. and s.c. injections of FG-4592.
Figure 4D:
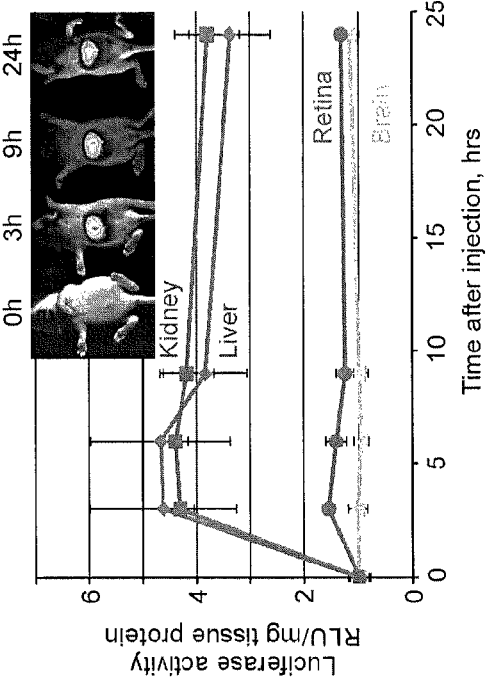
FIG. 4D is a graph of luciferase activity (RLU/mg tissue protein) in organ lysates derived from luc-ODD mice treated with FG-4592 as a function of time, and shows that PHD inhibition by FG-4592 gives sustained inhibition (HIF stabilization) over 24 hours.

Quantitation of the effect shown in FIG. 4A supports the specificity of this effect in tissue lysates. FIGS. 4B and 4C are graphs of luciferase activity (RLU/mg tissue protein) in organ-specific lysates derived from luc-ODD mice treated with PBS or FG-4592 by either s.c. or i.p. injection, and shows specificity of FG-4592 for liver and kidney. FIG. 4D depicts the results of a time course of HIF stabilization in kidney and lung, and shows that a single intraperitoneal injection of FG-4592 provides HIF PHD inhibition for at least 24 hours, with a half-life of 2-3 days.

The specificity of FG-4592 for liver and kidney was also demonstrated by immunoblot experiments. FIG. 5A is images of Western blots detecting HIF-1α protein in organ lysates derived from pups treated with PBS or FG-4592, and FIG. 5B is a graph of integrated optical density of the immunoblots shown in FIG. 5A. FIGS. 5A and 5B show that organ specific stabilization of HIF-1α protein results in a maximal increase in HIF-1α in liver and kidney lysates.

FIG. 5C is an image of a Western blot detecting HIF-1α in liver lysate derived from pups injected with FG-4592 and harvested after the indicated period of time, and the corresponding graph of integrated optical density of the immunoblot. The kinetics of HIF stabilization shown in FIG. 5C is similar to luminescence activity observed in the luc-ODD mouse (see FIG. 4D).

The kinetics of HIF stabilization also correlate with the kinetics of expression of erythropoietin (EPO), a gene product that HIF-1 regulates. FIG. 5E is a graph of EPO protein concentration in serum derived from pups injected with FG-4592 and harvested after the indicated period of time, and shows a correlation with the observed kinetics of HIF stabilization. FIG. 5D is a graph of organ-specific EPO mRNA expression in pups treated with PBS or FG-4592 by intraperitoneal injection.

A direct comparison of DMOG and FG-4592 in the oxygen induced retinopathy (OIR) model demonstrated that FG-4592 conferred at least the same benefit as DMOG, with a trend to superiority of FG-4592. FIG. 6A is images of flatmounts from pups receiving a sham PBS injection or an injection of DMOG or FG-4592 (top panel) and the corresponding flatmounts with computer-assisted area calculation to show the avascular region of the flatmounts at postnatal day 17 (P17) (bottom panel). The light-colored area in the flatmounts in the bottom panel indicates reduction of oxygen-induced vasoobliteration and protection due to FG-4592 or DMOG. FIG. 6B is a graph and shows the quantification and statistical analysis of the retinal flatmounts in the bottom panel of FIG. 6A, calculated as percent avascular area of total retinal area. FIGS. 6A and 6B show that treatment with FG-4592 and DMOG reduces capillary dropout 3-fold (p=0.001 for FG-4592) in retinal flatmounts when each is used in their optimal dose. FG-4592 requires less overall drug (10 µg/g FG-4592 versus 200 µg/g DMOG), which comprises about 3-fold reduction in drug molarity.

The effect of FG-4592 correlates to a reduction in ischemic hypoxic regions of retina when analyzed using a hypoxia sensitive probe. FIG. 6C is images of retinal flatmounts from pups receiving a sham PBS injection or an FG-4592 injection stained simultaneously for isolectin and Hypoxyprobe. Three representative replicates for each experimental condition are shown. FIG. 6C shows a decrease in ischemic, hypoxic retina at P17 after FG-4592 injection.

Figure 7B:
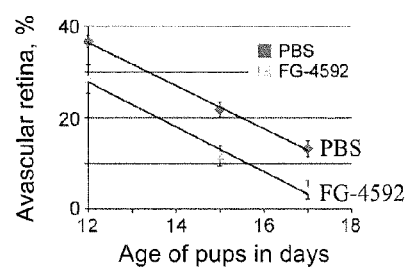
FIG. 7B is a graph of percentage of avascular retina as a function of age of pups, and shows the quantification of the avascular area depicted in FIG. 7A. The rate of retinal vascularization in PBS- and FG-4592-treated pups throughout the OIR cycle was calculated from the avascular area. The area of ischemia is less after FG-4592 treatment, yet the slopes of regrowth are identical between control and FG-4592-treated animals, indicating that FG-4592 protects retina during hyperoxia but does not induce abnormal or rapid regrowth of retinal blood vessels.
Figure 7A:
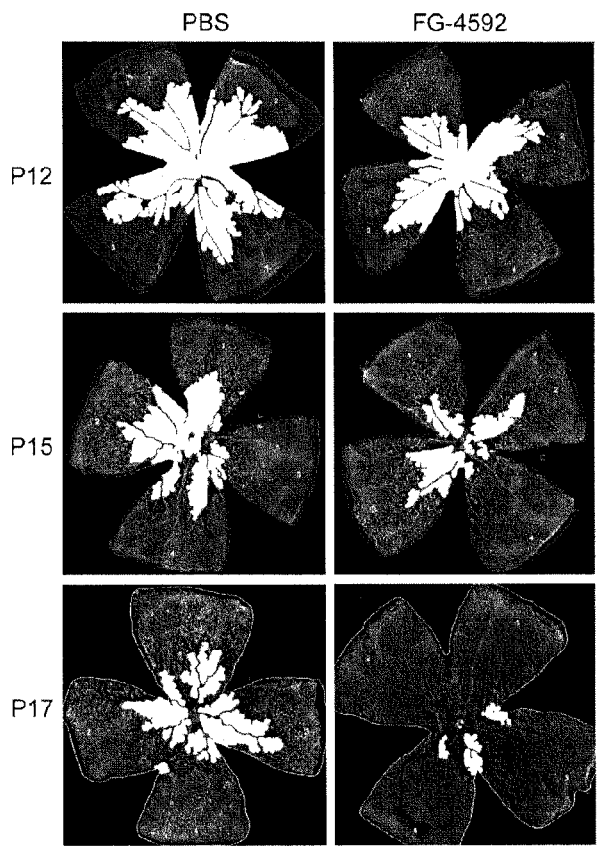
FIG. 7A is images of retinal flatmounts with computer-assisted area calculation from mouse pups at P12, P15 and P17 receiving PBS injections or FG-4592 injections.

The protective effect of FG-4592 was further studied to determine whether FG-4592 protected retinal blood vessels during hyperoxia or whether it facilitated regrowth in hypoxia. In order to assess the mechanism of the protective effect of FG-4592, retinal flatmounts were quantified at P12 (the end of hyperoxia), P15 (middle of hypoxia), and P17 (end of the OIR model). FIG. 7A is images of retinal flatmounts with computer-assisted area calculation from pups at P12, P15 and P17 receiving PBS injections or FG-4592 injections, and FIG. 7B is a graph of percentage of avascular retina as a function of age of pups, and shows the quantification of the avascular area depicted in FIG. 7A. Analysis of the change in central avascular region, which is the hallmark of vascular disease phenotype in mouse OIR, shows identical rates of decrease of this region in treated and untreated animals. The identical slope of retinovascular repair indicates that FG-4592 protects the retina from oxygen-induced vasoobliteration during hyperoxia rather than causing accelerated regrowth of vessels once out of hyperoxia. Therefore, HIF stabilization is a strategy that protects blood vessels from hyperoxic vasoobliteration.

Figure 8A:
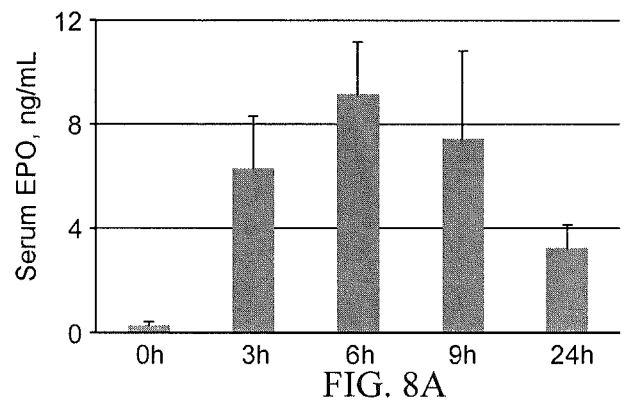
FIG. 8A is a graph of time-dependent changes in serum levels of EPO following FG-4592 treatment. Sera was collected at the indicated time points from P8 mouse pups injected with FG-4592. Protein levels of EPO were measured using an ELISA kit.
Figure 8B:
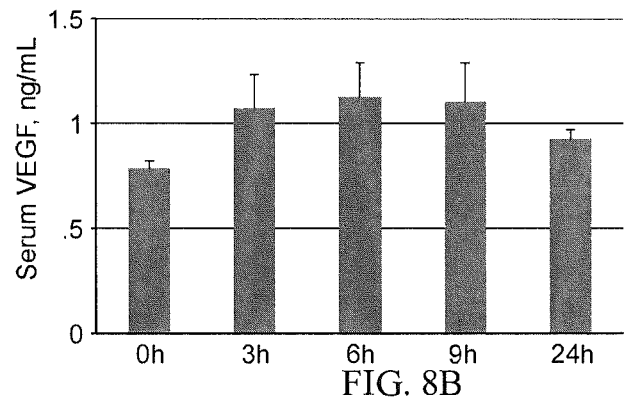
FIG. 8B is a graph of time-dependent changes in serum levels of VEGF following FG-4592 treatment. Sera was collected at the indicated time points from P8 mouse pups injected with FG-4592. Protein levels of VEGF were measured using an ELISA kit.
Figure 8C:
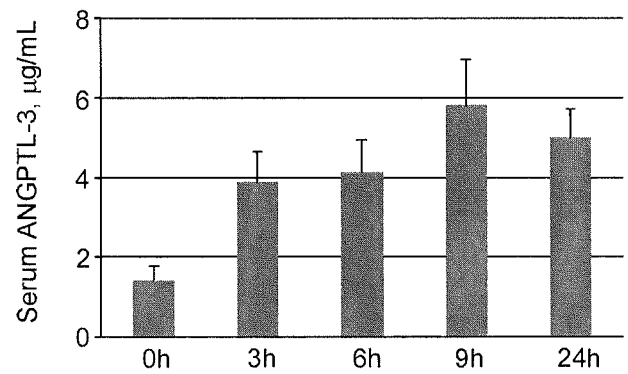
FIG. 8C is a graph of time-dependent changes in serum levels of angiopoietin-like protein 3 (ANGPTL-3) following FG-4592 treatment. Sera was collected at the indicated time points from P8 mouse pups injected with FG-4592. Protein levels of ANGPTL-3 were measured using an ELISA kit.

To identify hepatic intermediates that confer FG-4592-mediated protection of retinal capillaries, pro-angiogenic factors secreted by the liver in response to intraperitoneal injections of FG-4592 were studied. FIGS. 8A-8C are graphs of time-dependent changes in serum levels of angiogenic growth factors following FG-4592 treatment. In addition to the marked increase of circulating levels of EPO (FIG. 8A), FG-4592 treatment resulted in a moderate but statistically significant increase in serum levels of VEGF (FIG. 8B), as well as a 6-fold elevation of ANGPTL-3 in serum (FIG. 8C).

Hepatic EPO, VEGFA and ANGPTL3 mRNA levels and kinetics mirrored their corresponding serum protein concentrations (data not shown), supporting the notion of liver origin of the circulating pro-angiogenic growth factors. Time-course study revealed a time-dependent sequential upregulation of EPO, VEGF and ANGPTL-3. EPO production by the liver was transient, peaking at 3 hours after FG-4592 treatment, VEGF levels peaked at 6 hours after FG-4592 treatment, and ANGPTL-3, which is also associated with fatty acid and triglyceride transport, showed sustained induction, even 24 hours after FG-4592 treatment.

Discussion.

The use of small molecules, such as FG-4592, to stabilize a transcriptional activator, such as HIF, is a powerful technique for regulating gene expression noninvasively. Although not wishing to be bound by any particular theory, the liver specific secreted protein, ANGPTL-3, might underlie, at least in part, the mechanism of how a visceral organ is able to protect the retina. ANGPTL-3 is reported to be a liver specific secreted protein that regulates triglyceride metabolism through endothelial cell lipoprotein lipase inhibition, and also functions as an angiogenic factor through its interaction with integrins. The data described herein supports the use of ANGPTL-3 as a surrogate biomarker for FG-4592 efficacy; the studies described herein demonstrate that it is a specific hepatokine expressed in response to systemic FG-4592 resulting in sustained serum protein levels at 24 hours.

REFERENCES

1. S. T. Park A M, Maltepe E., Hypoxia-inducible factor (HIF) and HIF-stabilizing agents in neonatal care. *Semin Fetal Neonatal Med.* 15, 196 (Epub 2010 Jul. 4, 2010).
2. M. Ivan et al., HIFalpha targeted for VHL-mediated destruction by proline hydroxylation: implications for O2 sensing. *Science* 292, 464 (Apr. 20, 2001).
3. P. Jaakkola et al., Targeting of HIF-alpha to the von Hippel-Lindau ubiquitylation complex by O2-regulated prolyl hydroxylation. *Science* 292, 468 (Apr. 20, 2001).
4. F. Yu, S. B. White, Q. Zhao, F. S. Lee, HIF-1alpha binding to VHL is regulated by stimulus-sensitive proline hydroxylation. *Proceedings of the National Academy of Sciences of the United States of America* 98, 9630 (Aug. 14, 2001).
5. N. Masson, C. Willam, P. H. Maxwell, C. W. Pugh, P, J. Ratcliffe, Independent function of two destruction domains in hypoxia-inducible factor-alpha chains activated by prolyl hydroxylation. *The EMBO journal* 20, 5197 (Sep. 17, 2001).
6. A. C. Epstein et al., *C. elegans* EGL-9 and mammalian homologs define a family of dioxygenases that regulate. HIF by prolyl hydroxylation. *Cell* 107, 43 (Oct. 5, 2001).
7. R. K. Bruick, S. L. McKnight, A conserved family of prolyl-4-hydroxylases that modify HIF. *Science* 294, 1337 (Nov. 9, 2001).
8. G. L. Wang, G. L. Semenza, General involvement of hypoxia-inducible factor 1 in transcriptional response to hypoxia. *Proceedings of the National Academy of Sciences of the United States of America* 90, 4304 (May 1, 1993).
9. B. H. Jiang, E. Rue, G. L. Wang, R. Roe, G. L. Semenza, Dimerization, DNA binding, and transactivation properties of hypoxia-inducible factor 1. *Journal of Biological Chemistry* 271, 17771 (Jul. 26, 1996).
10. G. L. Semenza, Hypoxia-inducible factor 1: master regulator of O2 homeostasis. *Curr Opin Genet Dev* 8, 588 (October 1998).
11. G. L. Semenza, G. L. Wang, A nuclear factor induced by hypoxia via de novo protein synthesis binds to the human erythropoietin gene enhancer at a site required for transcriptional activation. *Molecular and Cellular Biology* 12, 5447 (December 1992).
12. D. J. Manalo et al., Transcriptional regulation of vascular endothelial cell responses to hypoxia by HIF-1. *Blood* 105, 659 (Jan. 15, 2005).
13. M. E. Hartnett, R. H. Lane, Effects of oxygen on the development and severity of retinopathy of prematurity. *Journal of AAPOS: the official publication of the American Association for Pediatric Ophthalmology and Strabismus/American Association for Pediatric Ophthalmology and Strabismus* 17, 229 (June 2013).
14. K. Claiborn, William G. Kaelin Jr. and Gregg L. Semenza receive the 2012 ASCI/Stanley J. Korsmeyer Award. *The Journal of clinical investigation* 122, 1136 (Apr. 2, 2012).
15. E. B. Rankin et al., Hypoxia-inducible factor-2 (HIF-2) regulates hepatic erythropoietin in vivo. *The Journal of clinical investigation* 117, 1068 (April 2007).
16. R. R. Ratan et al., Small molecule activation of adaptive gene expression: tilorone or its analogs are novel potent activators of hypoxia inducible factor-1 that provide prophylaxis against stroke and spinal cord injury. *Annals of the New York Academy of Sciences* 1147, 383 (December 2008).
17. A. Siddiq et al., Selective inhibition of hypoxia-inducible factor (HIF) prolyl-hydroxylase 1 mediates neuroprotection against normoxic oxidative death via HIF- and CREB-independent pathways. *The Journal of neuroscience: the official journal of the Society for Neuroscience* 29, 8828 (Jul. 8, 2009).
18. T. Eckle, D. Kohler, R. Lehmann, K. El Kasmi, H. K. Eltzschig, Hypoxia-inducible factor-1 is central to cardioprotection: a new paradigm for ischemic preconditioning. *Circulation* 118, 166 (Jul. 8, 2008).
19. C. Willam et al., HIF prolyl hydroxylases in the rat; organ distribution and changes in expression following hypoxia and coronary artery ligation. *Journal of molecular and cellular cardiology* 41, 68 (July 2006).
20. K. Sarkar, K. Fox-Talbot, C. Steenbergen, M. Bosch-Marce, G. L. Semenza, Adenoviral transfer of HIF-1alpha enhances vascular responses to critical limb ischemia in diabetic mice. *Proceedings of the National Academy of Sciences of the United States of America* 106, 18769 (Nov. 3, 2009).
21. J. E. Sears, G. Hoppe, Q. Ebrahem, B. Anand-Apte, Prolyl hydroxylase inhibition during hyperoxia prevents oxygen-induced retinopathy. *Proceedings of the National Academy of Sciences of the United States of America* 105, 19898 (Dec. 16, 2008).
22. H. Huang et al., Reduced retinal neovascularization, vascular permeability, and apoptosis in ischemic retinopathy in the absence of prolyl hydroxylase-1 due to the prevention of hyperoxia-induced vascular obliteration. *Investigative ophthalmology & visual science* 52, 7565 (September).
23. L. J. Duan, K. Takeda, G. H. Fong, Prolyl hydroxylase domain protein 2 (PHD2) mediates oxygen-induced retinopathy in neonatal mice. *The American journal of pathology* 178, 1881 (April).
24. W. V. Good, Final results of the Early Treatment for Retinopathy of Prematurity (ETROP) randomized trial. Trans Am Ophthalmol Soc 102, 233 (2004).
25. M. E. Hartnett and J. S. Penn. Mechanisms and management of retinopathy of prematurity. N Engl J Med. 367:2515-2526.
26. G. L. Semenza, M. K. Nejfelt, S. M. Chi, and S. E. Antonarakis. Hypoxia-inducible nuclear factors bind to an enhancer element located 3' to the human erythropoietin gene. Proceedings of the National Academy of Sciences of the United States of America. 88:5680-5684 (1991).
27. K. Takeda, A. Cowan, and G. H. Fong. Essential role for prolyl hydroxylase domain protein 2 in oxygen homeostasis of the adult vascular system. Circulation 116:774-781 (2007).
28. G. Trichonas, T. J. Lee, G. Hoppe, J. Au, and J. E. Sears. Prolyl hydroxylase inhibition during hyperoxia prevents oxygen-induced retinopathy in the rat 50/10 model, Investigative ophthalmology & visual science. 54:4919-4926 (2013).
29. G. Hoppe, T. J. Lee, S. Yoon, M. Yu, N. S. Peachey, M. Rayborn, M. J. Zutel, G. Trichonas, J. Au, and J. E. Sears. Inducing a Visceral Organ to Protect a Peripheral Capillary Bed: Stabilizing Hepatic HIF-1alpha Prevents Oxygen-Induced Retinopathy. The American journal of pathology (2014).
30. N. R. Rose, M. A. McDonough, O. N. King, A. Kawamura, and C. J. Schofield. Inhibition of 2-oxoglutarate dependent oxygenases. Chem Soc Rev. 40:4364-4397 (2011).
31. D. R. Mole, I. Schlemminger, L. A. McNeill, K. S. Hewitson, C. W. Pugh, P. J. Ratcliffe, and C. J. Schofield. 2-oxoglutarate analogue inhibitors of HIF prolyl hydroxylase. Bioorganic & medicinal chemistry letters. 13:2677-2680 (2003).
32. C. J. Schofieldand P. J. Ratcliffe. Oxygen sensing by HIF hydroxylases. Nat Rev Mol Cell Biol. 5:343-354 (2004).
33. J. E. Searsand G. Hoppe. Stimulating retinal blood vessel protection with hypoxia-inducible factor stabilization: identification of novel small-molecule hydrazones to inhibit hypoxia-inducible factor prolyl hydroxylase (an american ophthalmological society thesis). Transactions of the American Ophthalmological Society. 111:169-179 (2013).
34. M. Safran, Kim, W. Y., O'Connell, F., Flippin, L., Gunzler, V., Horner, J. W., Depinho, R. A., and Kaelin, W. G., Jr. Mouse model for noninvasive imaging of HIF prolyl hydroxylase activity: Assessment of an oral agent that stimulates erythropoietin production. Proc Natl Acad Sci USA. 103:105-110 (2006).
35. T. M. Asikainen, B. K. Schneider, N. S. Waleh, R. I. Clyman, W. B. Ho, L. A. Flippin, V. Gunzler, and C. W. White. Activation of hypoxia-inducible factors in hyperoxia through prolyl 4-hydroxylase blockade in cells and explants of primate lung. Proceedings of the National Academy of Sciences, USA. 102:10212-10217 (2005).
36. G. Camenisch, M. T. Pisabarro, D. Sherman, J. Kowalski, M. Nagel, P. Hass, M. H. Xie, A. Gurney, S. Bodary, X. H. Liang, K. Clark, M. Beresini, N. Ferrara, and H. P. Gerber. ANGPTL3 stimulates endothelial cell adhesion and migration via integrin alpha vbeta 3 and induces blood vessel formation in vivo. The Journal of biological chemistry. 277:17281-17290 (2002).
37. L. E. Smith, E. Wesolowski, A. McLellan, S. K. Kostyk, R. D'Amato, R. Sullivan, and P. A. D'Amore. Oxygen-induced retinopathy in the mouse. Investigative ophthalmology & visual science. 35:101-111 (1994).
38. K. M. Connor, N. M. Krah, R. J. Dennison, C. M. Aderman, J. Chen, K. I. Guerin, P. Sapieha, A. Stahl, K. L. Willett, and L. E. Smith. Quantification of oxygen-induced retinopathy in the mouse: a model of vessel loss, vessel regrowth and pathological angiogenesis. Nat Protoc. 4:1565-1573 (2009).
39. A. Stahl, K. M. Connor, P. Sapieha, K. L. Willett, N. M. Krah, R. J. Dennison, J. Chen, K. I. Guerin, and L. E. Smith. Computer-aided quantification of retinal neovascularization. Angiogenesis. 12:297-301 (2009).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claim.

What is claimed is:

1. A method of treating retinopathy of prematurity in a premature and/or low birth weight infant in need thereof, the method comprising administering to the infant an effective amount of a compound represented by Structural Formula II:

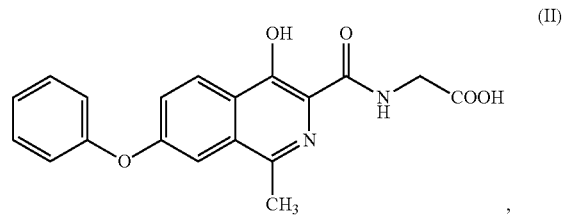 [SMILES: Cc1nc(C(=O)NCC(=O)O)c(O)c2ccc(Oc3ccccc3)cc12]

or a pharmaceutically acceptable salt thereof.

2. The method of claim 1, wherein the compound, or pharmaceutically acceptable salt thereof, is administered during phase I of retinopathy of prematurity.

3. The method of claim 1, wherein the compound, or pharmaceutically acceptable salt thereof, is administered while the infant is in a hyperoxic state.

4. The method of claim 1, wherein the infant is a premature infant.

5. The method of claim 1, wherein the infant is a low birth weight infant.

6. The method of claim 1, wherein the compound, or pharmaceutically acceptable salt thereof, is administered during about the first 14 to about the first 28 days of the infant's life.

7. The method of claim 1, wherein the compound, or pharmaceutically acceptable salt thereof, is administered at about 3 to about 7 day intervals.

8. The method of claim 1, further comprising administering supplemental oxygen to the premature and/or low birth weight infant.

9. The method of claim 1, the method comprising:
administering to the infant an effective amount of a compound represented by Structural Formula II:

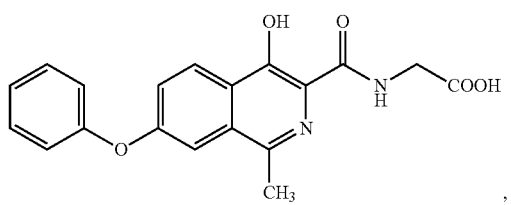

(II)

or a pharmaceutically acceptable salt thereof, during phase I of retinopathy of prematurity; and further administering supplemental oxygen to the infant.

10. The method of claim 1, wherein the infant is a severely premature infant.

11. The method of claim 1, wherein the compound, or pharmaceutically acceptable salt thereof, is administered systemically.

12. The method of claim 11, wherein the compound, or pharmaceutically acceptable salt thereof, is administered intraperitoneally, intravenously or subcutaneously.

13. The method of claim 11, wherein the compound, or pharmaceutically acceptable salt thereof, is administered orally.

14. The method of claim 6, wherein the compound, or pharmaceutically acceptable salt thereof, is administered during about the first 16 days of the infant's life.

15. The method of claim 6, wherein the compound, or pharmaceutically acceptable salt thereof, is administered during about the first 21 to about the first 28 days of the infant's life.

16. The method of claim 7, wherein the compound, or pharmaceutically acceptable salt thereof, is administered every four days.

17. The method of claim 7, wherein the compound, or pharmaceutically acceptable salt thereof, is administered every seven days.

18. The method of claim 8, wherein an oxygen saturation level of about 90% to about 95% is maintained in the premature and/or low birth weight infant.

* * * * *